(12) United States Patent
Kubota et al.

(10) Patent No.: US 12,370,104 B2
(45) Date of Patent: Jul. 29, 2025

(54) BED APPARATUS

(71) Applicant: Paramount Bed Co., Ltd., Tokyo (JP)

(72) Inventors: Shinnosuke Kubota, Tokyo (JP); Tatsuya Shimada, Tokyo (JP); Masato Shimokawa, Tokyo (JP); Toshihide Shiino, Tokyo (JP)

(73) Assignee: Paramount Bed Co., Ltd., Tokyo (JP)

( * ) Notice: Subject to any disclaimer, the term of this patent is extended or adjusted under 35 U.S.C. 154(b) by 1103 days.

(21) Appl. No.: 17/050,058

(22) PCT Filed: May 10, 2019

(86) PCT No.: PCT/JP2019/018767
§ 371 (c)(1),
(2) Date: Oct. 23, 2020

(87) PCT Pub. No.: WO2020/115924
PCT Pub. Date: Jun. 11, 2020

(65) Prior Publication Data
US 2021/0085547 A1 Mar. 25, 2021

(30) Foreign Application Priority Data
Dec. 5, 2018 (JP) ................. 2018-228590

(51) Int. Cl.
*A61G 7/018* (2006.01)
*A47C 19/04* (2006.01)
(Continued)

(52) U.S. Cl.
CPC .............. *A61G 7/018* (2013.01); *A61B 5/024* (2013.01); *A61B 5/08* (2013.01); *A61B 5/1115* (2013.01);
(Continued)

(58) Field of Classification Search
CPC .......... A61G 7/018; A61G 7/05; A61G 7/015; A61G 7/012; A61G 7/0524; A61G 7/052;
(Continued)

(56) References Cited

U.S. PATENT DOCUMENTS 6,353,949 B1 * 3/2002 Falbo ................. A61G 13/04
5/624
2010/0223724 A1 * 9/2010 Niwa .................. A61G 7/0573
5/412

(Continued)

FOREIGN PATENT DOCUMENTS

CN 104188638 A 12/2014
CN 205054682 U 3/2016
(Continued)

OTHER PUBLICATIONS

International Search Report PCT/ISA/210 for International Application No. PCT/JP2019/018767 Dated Aug. 13, 2019.
(Continued)

*Primary Examiner* — Justin C Mikowski
*Assistant Examiner* — Morgan J McClure
(74) *Attorney, Agent, or Firm* — Harness, Dickey & Pierce, P.L.C.

(57) ABSTRACT

A high-performance bed apparatus is provided. The bed apparatus includes a supporting unit that supports a user, and a control unit that controls an operation of the supporting unit, wherein a speed of the operation of the supporting unit in a case where the user manipulates the supporting unit is higher than a speed at which the control unit automatically causes the supporting unit to operate.

24 Claims, 16 Drawing Sheets

(51) Int. Cl.
  *A47C 20/08* (2006.01)
  *A61B 5/024* (2006.01)
  *A61B 5/08* (2006.01)
  *A61B 5/11* (2006.01)
  *A61G 7/012* (2006.01)
  *A61G 7/05* (2006.01)
  *A61G 13/02* (2006.01)

(52) U.S. Cl.
  CPC .............. *A61B 5/1116* (2013.01); *A61G 7/05* (2013.01); *A47C 19/04* (2013.01); *A47C 20/08* (2013.01); *A61G 7/012* (2013.01); *A61G 13/02* (2013.01); *A61G 2203/10* (2013.01); *A61G 2203/36* (2013.01)

(58) Field of Classification Search
  CPC .. A61G 7/0521; A61G 7/1063; A61G 7/1065; A61G 7/1067; A61G 13/02; A61G 13/06; A61G 13/08; A61G 13/04; A61G 2203/10; A61G 2203/36; A61G 2203/16; A61G 2203/14; A61G 2203/12; A61G 2203/20; A61G 2203/22; A61G 2203/74; A61B 5/024; A61B 5/08; A61B 5/1115; A61B 5/1116; A61B 5/0816; A61B 5/1114; A61B 5/4809; A61B 5/6892; A47C 19/04; A47C 19/045; A47C 20/08; A47C 20/041; A47C 20/04; A47C 31/008
  See application file for complete search history.

(56) References Cited

U.S. PATENT DOCUMENTS

| | | | | |
|---|---|---|---|---|
| 2011/0277235 | A1* | 11/2011 | Okumatsu | A61G 7/1017 5/83.1 |
| 2016/0066703 | A1* | 3/2016 | Chen | A47C 31/00 5/613 |
| 2016/0128610 | A1* | 5/2016 | Kostic | A61G 13/04 5/613 |
| 2017/0143565 | A1* | 5/2017 | Childs | A61G 7/015 |
| 2017/0172827 | A1* | 6/2017 | Schaaf | A61G 5/006 |
| 2018/0184984 | A1 | 7/2018 | Zerhusen et al. | |
| 2018/0338625 | A1* | 11/2018 | Nava | A47C 19/021 |
| 2020/0113760 | A1 | 4/2020 | Yoshida et al. | |
| 2024/0032860 | A1* | 2/2024 | Rao | G16H 15/00 |

FOREIGN PATENT DOCUMENTS

| | | |
|---|---|---|
| JP | H09220262 A | 8/1997 |
| JP | 2004-159804 A | 6/2004 |
| JP | 2004-159808 A | 6/2004 |
| JP | 2004-159809 A | 6/2004 |
| JP | 2008-259630 A | 10/2008 |
| JP | 2012-34979 A | 2/2012 |
| JP | 2016-5518 A | 1/2016 |
| JP | 2016-55150 A | 4/2016 |
| JP | 2017-86269 A | 5/2017 |
| JP | 6416984 B1 | 10/2018 |
| JP | 2018-187022 A | 11/2018 |

OTHER PUBLICATIONS

Chinese Office Action and English translation thereof dated Apr. 11, 2022.

Chinese Office Action and English translation thereof dated Jan. 13, 2022.

Singapore Office Action mailed Apr. 1, 2022.

International Preliminary Report on Patentability dated Jun. 17, 2021.

Japanese Office Action and English translation thereof dated Dec. 14, 2021.

Office Action dated May 17, 2022 issued in corresponding Japanese Patent Application No. 2018-228590.

* cited by examiner

BED APPARATUS

TECHNICAL FIELD

The present embodiment relates to a bed apparatus.

BACKGROUND ART

There is known a bed apparatus including a plurality of sections, which supports the load of a user P or a person requiring care, and a plurality of driving units, which adjusts the position of each section. In such a bed apparatus, operating each driving unit enables adjusting the position of each section and thus appropriately supporting the body of a user (user P or person requiring care). To enable the bed apparatus to adjust the position of each section, it is conceivable to employ, for example, an actuator as a driving unit (for example, see Patent Literature 1).

PRIOR ART LITERATURE

Patent Literature

Patent Literature 1: JP-A-09-220262

SUMMARY OF THE INVENTION

Problems that the Invention is to Solve

A high-performance bed apparatus is provided.

Means for Solving the Problems

A bed apparatus according to an embodiment includes a supporting unit that supports a user, and a control unit that controls an operation of the supporting unit, wherein a speed of the operation of the supporting unit in a case where the user manipulates the supporting unit is higher than a speed at which the control unit automatically causes the supporting unit to operate.

MODE FOR CARRYING OUT THE INVENTION

Figure 1:
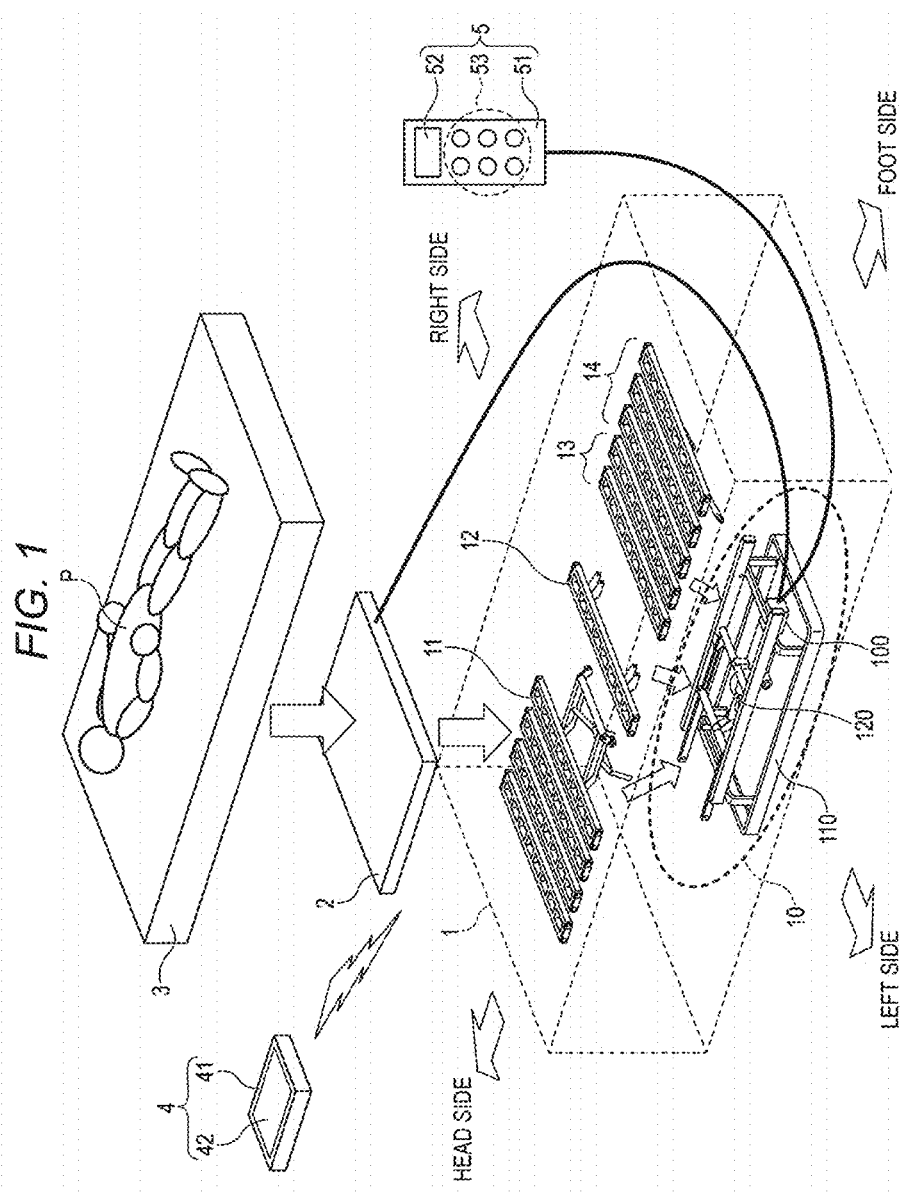
FIG. 1 is a diagram structurally illustrating a bed system including a bed apparatus.

Hereinafter, details of embodiments are described with reference to the drawings. In this description, over all of the figures, portions which are in common are assigned the respective reference characters which are in common.

<1> First Embodiment

<1-1> Configuration

<1-1-1> Bed System

Figure 2:
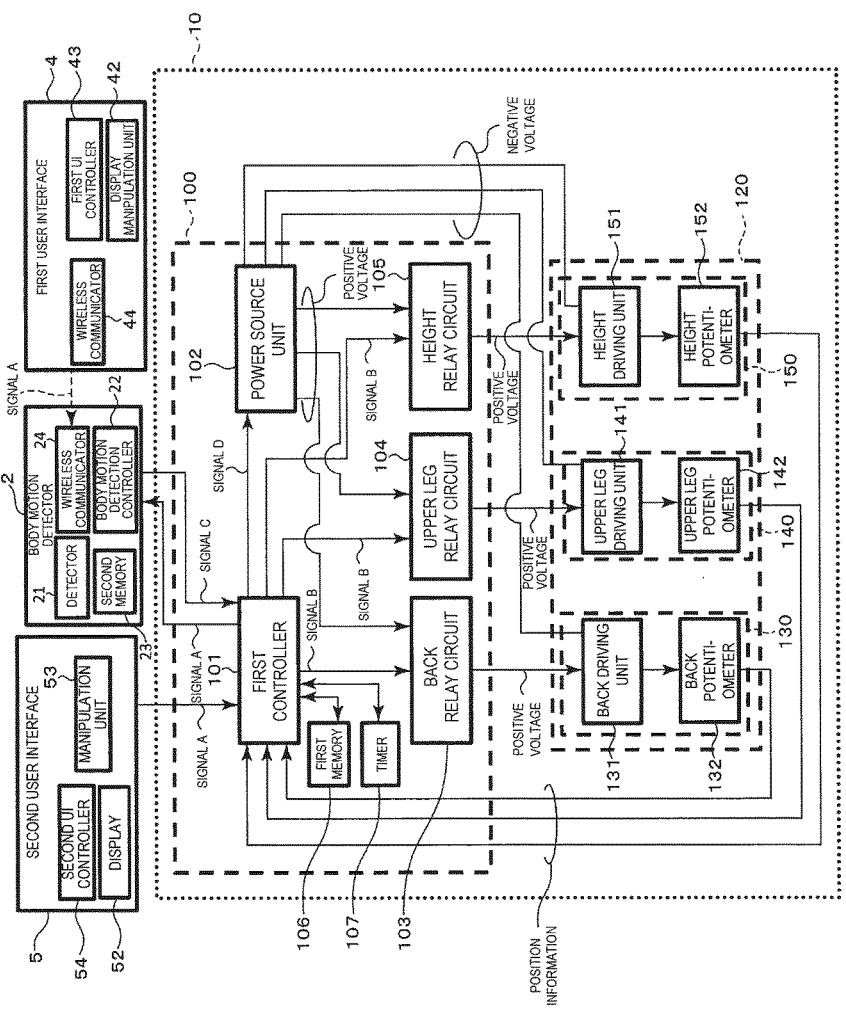
FIG. 2 is a diagram functionally illustrating the bed system including the bed apparatus.

A bed system including a bed apparatus is described with use of FIG. 1 and FIG. 2. FIG. 1 is referred to when a structural description is made, and FIG. 2 is referred to when a functional description is made.

As illustrated in FIG. 1, the bed system includes a bed apparatus 1, a body motion detector 2, a mattress 3, a first user interface 4, and a second user interface 5. The mattress 3 is provided on the bed apparatus 1, and the body motion detector 2 is provided between the bed apparatus 1 and the mattress 3.

As illustrated in FIG. 1, the bed apparatus 1 includes a base 10, a back section 11, a seat section 12, an upper leg section 13, and a lower leg section 14.

For explanatory convenience, in the mattress 3, an end portion close to the head of a user P and an end portion close to the toes of the user P are referred to as a "head-side end portion" and a "foot-side end portion", respectively. With reference to a case where the user P lies on the mattress 3 in the supine position, a portion on the right side of the user P is referred to as a "right-side portion" and a portion on the left side of the user P is referred to as a "left-side portion". This also applies to the bed apparatus 1.

From the head side of the base 10 toward the foot side thereof, the back section (first section) 11, the seat section (second section) 12, the upper leg section (third section) 13, and the lower leg section (fourth section) 14 are arranged in sequence. While, in the present embodiment, the bed apparatus 1 includes the first to fourth sections, the present embodiment is not limited to this, and the second section does not need to be provided or what is called a kyma (κύμα) (a Greek word meaning wave) line can also be employed.

The back section 11 supports the load of the head to the back of the user. The seat section 12 supports the load of the lower back of the user. The upper leg section 13 supports the load of the lower back to the knee of the user. The lower leg section 14 supports the load of the knee to the foot of the user.

Furthermore, in a case where it is not necessary to distinguish the back section 11, the seat section 12, the upper leg section 13, and the lower leg section 14 from one another, those sections are merely referred to as a "section (supporting unit)".

The base 10 includes a control box 100, a frame 110, and a movement unit 120.

The frame 110 is a metallic frame which supports the back section 11, the seat section 12, the upper leg section 13, and the lower leg section 14.

The control box 100 causes the movement unit 120 to operate in such a way as to change the positions (angles or heights) of the respective sections.

The movement unit 120 changes the positions (angles or heights) of the respective sections based on signals and voltages supplied from the control box 100. While, in the present embodiment, the movement unit 120 is configured to change the positions of the respective sections, the present embodiment is not limited to this, and, for example, the movement unit 120 can be configured to be also able to change the position (angle or height) of the frame 110.

The body motion detector 2 and the second user interface 5 are connected to the control box 100 via a wired connection. The control box 100 operates in response to signals being received from the body motion detector 2 and the second user interface 5.

The body motion detector 2 determines the state of the user P. Specifically, when the user P goes to bed, the body motion detector 2 detects body motion (vibration) of the user P via the mattress 3. Then, the body motion detector 2 is able to determine whether the user is waking, whether the user is sleeping, or whether the user is out of bed or in bed (also referred to as "out-of-bed or in-bed"). The employable method of detecting such an out-of-bed state, in-bed state, position, and posture of the user P includes, for example, a method for detecting getting-in and getting-out described in Japanese Patent Application No. 2002-327624 (the title of the invention: device for detecting getting in and getting out of bed, and the application date: Nov. 11, 2002), a method for detection described in Japanese Patent Application No. 2002-327632 (the title of the invention: device for detecting positional deviation on bed, and the application date: Nov. 11, 2002), and a method for detection described in Japanese Patent Application No. 2002-327633 (the title of the invention: device for detecting position on bed, and the application date: Nov. 11, 2002). The contents of these patent applications are incorporated by reference herein in their entirety.

Moreover, the body motion detector 2 is also able to determine the heartbeat rate and respiratory rate of the user based on the detected body motion. Moreover, the body motion detector 2 is able to determine whether the user is present on the mattress 3 or is not present thereon. The state in which the user is present on the mattress 3 is referred to as "in-bed". The state in which the user is not present on the mattress 3 is referred to as "out-of-bed".

The body motion detector 2 operates in response to a signal being wirelessly received from the first user interface 4.

The bed system is described in a functional manner with use of FIG. 2.

As illustrated in FIG. 2, the control box 100 includes a first controller 101, a power source unit 102, a back relay circuit 103, an upper leg relay circuit 104, a height relay circuit 105, a first memory 106, and a timer 107. In a case where it is not necessary to distinguish the back relay circuit 103, the upper leg relay circuit 104, and the height relay circuit 105 from one another, these circuits are merely referred to as a "relay circuit".

The movement unit 120 includes a first actuator 130, a second actuator 140, and a third actuator 150. The first actuator 130 includes a back driving unit 131 and a back potentiometer 132. The second actuator 140 includes an upper leg driving unit 141 and an upper leg potentiometer 142. The third actuator 150 includes a height driving unit 151 and a height potentiometer 152. Furthermore, in a case where it is not necessary to distinguish the first actuator 130, the second actuator 140, and the third actuator 150 from one another, these actuators are merely referred to as an "actuator". Moreover, in a case where it is not necessary to distinguish the back driving unit 131, the upper leg driving unit 141, and the height driving unit 151 from one another, these driving units are merely referred to as a "driving unit". Moreover, in a case where it is not necessary to distinguish the back potentiometer 132, the upper leg potentiometer 142, and the height potentiometer 152 from one another, these potentiometers are merely referred to as a "potentiometer".

The body motion detector 2 includes a detector 21, a body motion detection controller 22, a second memory 23, and a wireless communicator 24.

The first user interface 4 includes a display manipulation unit 42, a first UI controller 43, and a wireless communicator 44.

The first user interface 4 is, for example, a tablet, a smartphone, or a personal computer (PC). The first UI controller 43 displays an application on the display manipulation unit 42. The user selects an instruction directed to the bed system via the application displayed on the display manipulation unit 42. The wireless communicator 44 transmits the instruction directed to the bed system as a signal A to the body motion detector 2.

The detector 21 of the body motion detector 2 detects the body motion (vibration) of the user P such as that mentioned above. The body motion detection controller 22 of the body motion detector 2 is able to determine the state of the user based on the detected body motion (vibration). Information associated with the signal A is stored in the second memory 23 of the body motion detector 2. The wireless communicator 24 receives the signal A from the first user interface 4. Upon receiving the signal A, the body motion detection controller 22 refers to the second memory 23 and then reads out therefrom information indicating a "first state of the user" corresponding to the signal A. Then, the body motion detection controller 22 detects whether the state of the user is the first state based on the read-out information. Then, the body motion detection controller 22 supplies a result of such detection as a signal C to the control box 100.

The first memory 106 of the control box 100 stores various pieces of information. Specifically, the first memory 106 stores information concerning the signal C, and is accessed by the first controller 101. Moreover, the first memory 106 stores position information which is supplied from the potentiometer.

The timer 107 performs time counting (measurement of time) in response to an instruction from the first controller 101.

The first controller 101 controls the control box 100 based on the signal C supplied from the body motion detector 2. Specifically, upon receiving the signal C, the first controller 101 accesses the first memory 106, reads out therefrom movement information corresponding to the signal C, and then supplies a signal B to the relay circuit and supplies a signal D to the power source unit 102 based on the read-out movement information. The first controller 101 monitors the value of a current flowing through the actuator. For example, when determining that the value of a current flowing through the actuator exceeds a predetermined value (stored in the first memory 106), the first controller 101 determines that, for example, a load is being applied to the section.

The power source unit 102 transfers a voltage having a first polarity (for example, positive polarity) to the relay circuit and transfers a voltage having a second polarity (for example, negative polarity) to the actuator based on the signal D supplied from the first controller 101. Furthermore, the power source unit 102 can receive not only electric power supplied from an external source but also electric power supplied from, for example, a battery or a manually-operated electric generator.

The back relay circuit 103 electrically interconnects the back driving unit 131 and the power source unit 102 based on the signal B supplied from the first controller 101. This causes a positive voltage to be supplied to the back driving unit 131. The upper leg relay circuit 104 electrically interconnects the upper leg driving unit 141 and the power source unit 102 based on the signal B supplied from the first controller 101. This causes a positive voltage to be supplied to the upper leg driving unit 141. The height relay circuit 105 electrically interconnects the height driving unit 151 and the power source unit 102 based on the signal B supplied from the first controller 101. This causes a positive voltage to be supplied to the height driving unit 151.

The back driving unit 131 operates in response to a first voltage and a second voltage being supplied thereto.

The back potentiometer 132 detects the state of the back driving unit 131, and then transmits the detected state as position information to the control box 100. The first memory 106 stores the received position information. Furthermore, this position information is able to be handled as position information about the back section.

The same applies to the other driving units and potentiometers.

While, here, the bed system being controlled via the first user interface 4 has been described, the present embodiment is not necessarily limited to this. Specifically, as illustrated in FIG. 2, the bed system can be controlled via the second user interface 5. The second user interface 5 as used herein is a controller for the control box 100, which is called, for example, a hand-held remote switch. The second user interface 5 includes a display 52, a manipulation unit 53, and a second UI controller 54. The user selects an instruction directed to the bed system via a screen displayed on the display 52 and via the manipulation unit 53. The second UI controller 54 transmits the instruction directed to the bed system as a signal A to the control box 100. Upon receiving the signal A from the second user interface 5, the first controller 101 transfers the signal A to the body motion detector 2. This enables the body motion detector 2 to operate based on the signal A.

Figure 3:
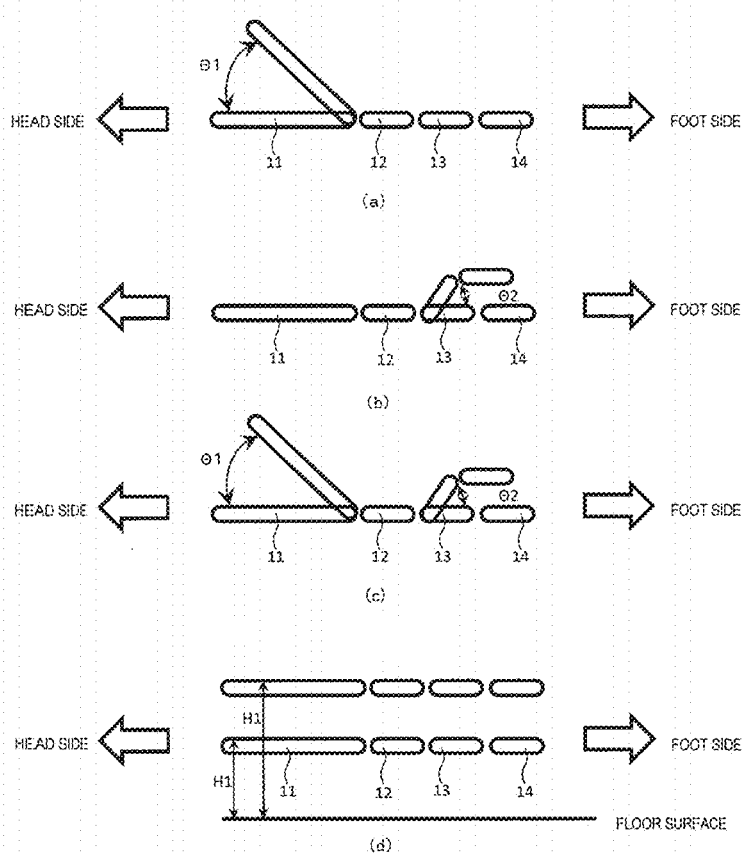
FIG. 3 is a diagram illustrating movements of sections.

Next, the motion of each section is described with reference to FIG. 3.

As illustrated in FIG. 3(a), the back driving unit 131 inclines the back section 11 with respect to a floor surface on which the base 10 is mounted. The operation to increase an inclination angle (back angle) θ1 between the back section 11 and the floor surface is referred to as a "back raising (or head raising)" operation, and the operation to decrease the inclination angle θ1 is referred to as a "back lowering (or head lowering)" operation.

As illustrated in FIG. 3(b), the upper leg driving unit 141 inclines the upper leg section 13 with respect to the floor surface. The operation to increase an inclination angle θ2 between the upper leg section 13 and the floor surface is referred to as an "upper leg raising (or foot raising)" operation, and the operation to decrease the inclination angle θ2 is referred to as an "upper leg lowering (or foot lowering)" operation.

As illustrated in FIG. 3(b), the lower leg section 14 operates in interlocking with the upper leg section 13.

Furthermore, as illustrated in FIG. 3(c), "back raising" and "foot raising" can operate in interlocking with each other. Such an operation is referred to as "interlocking raising". Likewise, "back lowering" and "foot lowering" can operate in interlocking with each other. Such an operation is referred to as "interlocking lowering".

As illustrated in FIG. 3(d), with respect to the back section 11, the seat section 12, the upper leg section 13, and the lower leg section 14, the height H1 of the upper surface of the section, on which the mattress 3 is placed, from the floor surface is changed by the height driving unit 151. An operation to increase the height H1 is referred to as a "height raising" operation, and an operation to decrease the height H1 is referred to as a "height lowering" operation.

Furthermore, the "raising" operation means at least one operation of the "back raising (or head raising)" operation, the "upper leg raising (or foot raising)" operation, and the "height raising" operation. Moreover, the "lowering" operation means at least one operation of the "back lowering (or head lowering)" operation, the "upper leg lowering (or foot lowering)" operation, and the "height lowering" operation.

<1-1-2> First User Interface

Figure 4:
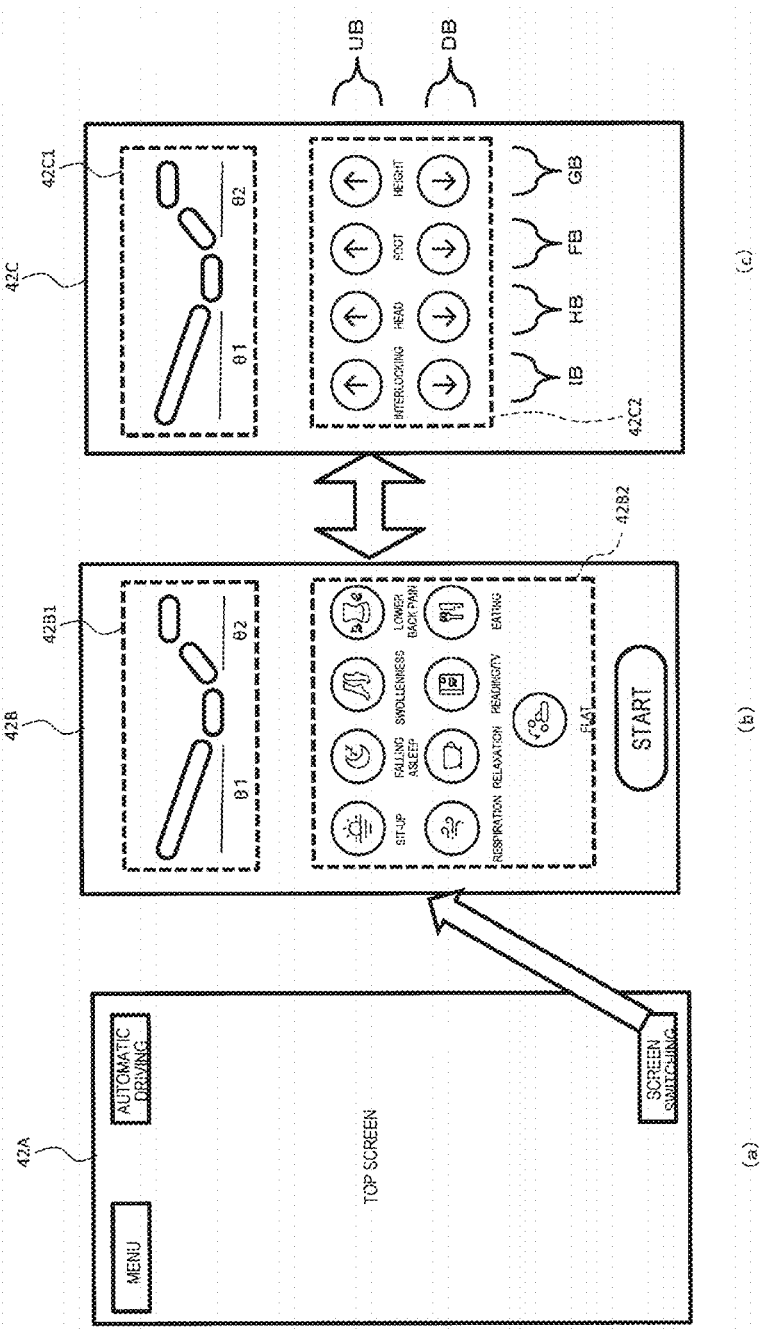
FIG. 4 illustrates examples of screens each of which is displayed on a display manipulation unit of a first user interface.
Figure 5:
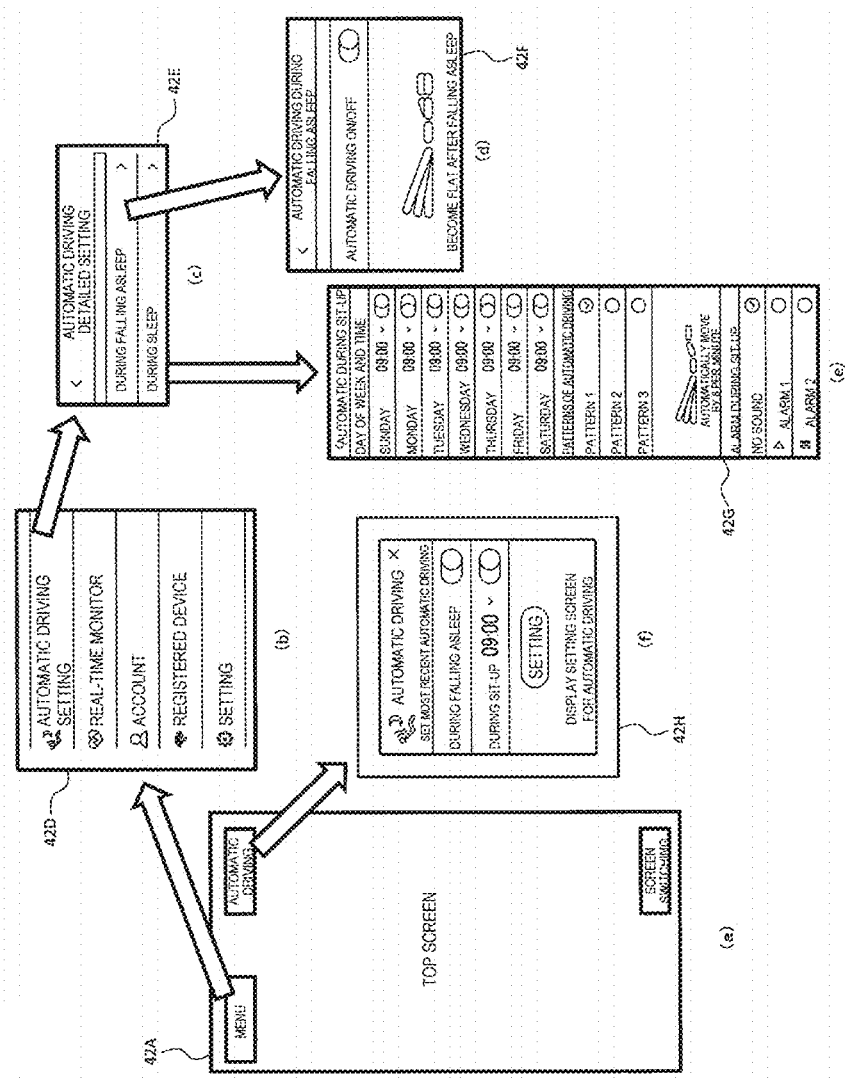
FIG. 5 illustrates examples of screens each of which is displayed on the display manipulation unit of the first user interface.

Next, screens each of which is displayed on the display manipulation unit 42 of the first user interface 4 are described with use of FIG. 4 and FIG. 5.

The first UI controller 43 displays an optional manipulation screen on the display manipulation unit 42 based on an application. For simplicity, FIG. 4 and FIG. 5 illustrate only screens each of which is displayed on the display manipulation unit 42.

FIG. 4(a) illustrates a screen 42A which is displayed on the display manipulation unit 42. The screen 42A is, for example, a top screen, and shows, for example, an icon ("menu") for transitioning to a screen concerning a menu of the bed system, an icon ("automatic driving") for transitioning to a screen concerning setting of automatic driving of the bed system, and an icon ("screen switching") for switching to a screen concerning a manipulation of the bed apparatus 1. The screen 42A can also show icons other than these three icons.

When determining that the icon of "screen switching" in the screen 42A has been selected by the user, the first UI controller 43 causes the screen 42A to transition to a screen 42B (FIG. 4(b)).

As illustrated in FIG. 4(b), the screen 42B is a screen concerning a manipulation of the bed apparatus 1, and shows a field 42B1, which indicates information about the position of each section and the position of the frame in the bed apparatus 1, a field 42B2, which shows a plurality of icons for selecting an operation mode of the bed apparatus 1, and an icon ("START"), which is operable to execute the mode selected via the field 42B2. The field 42B1 shows a schematic view, which indicates the current position of each section and the current position of the frame in the bed apparatus 1, the inclination angle θ1, and the inclination angle θ2. When determining that any one of icons concerning postures classified by purpose in the field 42B2 ("sit-up", "falling asleep", "swollenness", "lower back pain", "respiration", "relaxation", "reading/TV", "eating", and "flat") has been selected by the user and, then, the icon of "START" has been selected, the first UI controller 43 instructs the bed apparatus 1 to execute the selected operation mode. Moreover, in the case of determining that the screen 42B has been swiped by the user, the first UI controller 43 causes the screen 42B to transition to a screen 42C (FIG. 4(c)).

Furthermore, purposes and postures in the respective icons in the field 42B2 are set as follows.

The icon of "sit-up" is an icon used to set aback raising posture (for example, the inclination angle $\theta 1=X1°$), which is used when, after waking up in the morning, the user P rises up in the bed.

The icon of "falling asleep" is an icon used to set a state in which the back is raised to prompt falling asleep of the user P (a posture for easier respiration or for easier relaxation (for example, the inclination angle $\theta 1=X2°$)).

The icon of "swollenness" is an icon used to set a state in which the upper leg is raised to reduce the swollenness of the leg of the user P.

The icon of "lower back pain" is an icon used to set a state in which the back is raised to reduce the load on the lower back of the user P (a posture for prompting relaxation of the iliopsoas muscle (for example, the inclination angle $\theta 1=X3°$)).

The icon of "respiration" is an icon used to set a state in which the back is raised which is said to be easy for respiration and have an apnea reducing effect (for example, the inclination angle $\theta 1=X4°$).

The icon of "relaxation" is an icon used to set a state in which the back is raised and the upper leg is also raised which is supposed to be easy for respiration and be a 0 G position in which the user is less likely to feel stress (an ideal sleeping posture such as that in zero gravity) (for example, the inclination angles $\theta 1=X5°$ and $\theta 2=X6°$).

The icon of "reading/TV" is an icon used to set a state of the bed available for reading or TV viewing (for example, the inclination angles $\theta 1=X7°$ and $\theta 2=X8°$).

The icon of "eating" is an icon used to set a state which is nearly equal to a chair used when the user eats in bed (for example, the inclination angle $\theta 1=X9°$).

The icon of "flat" is an icon used to set the inclination angles $\theta 1=0°$ and $\theta 2=0°$.

As illustrated in FIG. 4(c), a screen 42C is a screen concerning a manipulation, and shows a field 42C1, which indicates the position of each section and the position of the frame in the bed apparatus 1, and a field 42C2, which is used to manipulate the bed apparatus 1. The field 42C1 is similar to the field 42B1. A plurality of icons, which is used to manipulate the bed apparatus 1, is shown in the field 42C2. Specifically, in the field 42C2, icons labelled with UB are associated with the "raising" operation. Icons labelled with DB are associated with the "lowering" operation. Icons labelled with IB are associated with "interlocking". Icons labelled with HB are associated with "head (back)". Icons labelled with FB are associated with "foot (upper leg)". Icons labelled with GB are associated with "height". The first UI controller 43 instructs the bed apparatus 1 to perform a "raising" or "lowering" operation in response to each icon being selected by the user.

As illustrated in FIG. 5(a), when determining that the icon of "menu" in the screen 42A has been selected by the user, the first UI controller 43 causes the screen 42A to transition to a screen 42D (FIG. 5(b)). Moreover, when determining that the icon of "automatic driving" in the screen 42A has been selected by the user, the first UI controller 43 causes the screen 42A to transition to a screen 42H (FIG. 5(f)).

As illustrated in FIG. 5(b), the screen 42D is a screen concerning a menu of the bed system, in which optional items are shown. Examples of the items include an icon ("automatic driving setting") used for transitioning to a screen concerning detailed settings of automatic driving of the bed system, an icon ("real-time monitor") used for transitioning to a screen indicating the state of the user P which is obtained from the body motion detector 2, an icon ("account") used for transitioning to a screen related to an account allocated to the user, an icon ("registered device") used for transitioning to a screen indicating devices registered with the bed system, and an icon ("setting") used for transitioning to a screen indicating various settings of the bed system. When determining that the icon of "automatic driving setting" in the screen 42D has been selected by the user, the first UI controller 43 causes the screen 42D to transition to a screen 42E (FIG. 5(c)).

As illustrated in FIG. 5(c), the screen 42E is a screen concerning automatic driving setting of the bed system, in which an item related to "during falling asleep" or "during sit-up" is shown. When determining that the icon of "during falling asleep" in the screen 42E has been selected by the user, the first UI controller 43 causes the screen 42E to transition to a screen 42F (FIG. 5(d)). Moreover, when determining that the icon of "during sit-up" in the screen 42E has been selected by the user, the first UI controller 43 causes the screen 42E to transition to a screen 42G (FIG. 5(e)).

As illustrated in FIG. 5(d), the screen 42F is a screen used to select whether to turn on or off automatic driving during falling asleep.

As illustrated in FIG. 5(e), the screen 42G is a screen used to set automatic driving during sit-up. The screen 42G is able to be used to set, for example, sit-up scheduled time for the user, an operation pattern of the bed apparatus 1 during sit-up, and the presence or absence of an alarm during sit-up.

As illustrated in FIG. 5(f), the screen 42H is a screen used to perform setting of most recent automatic driving.

While, here, the first user interface 4 has been described, with respect to the second user interface 5, similar operations can also be performed.

Moreover, in the first user interface 4 or the second user interface 5, a speed at which to move the bed apparatus 1 in the automatic driving mode can be set lower than a speed at which to move the bed apparatus 1 in response to the user P selecting an icon related to the "raising" operation or an icon related to the "lowering" operation. In other words, the speed of operation of the section in a case where the user P manipulates the bed apparatus 1 is higher than a speed at which the bed system automatically causes the section to operate (automatic driving mode).

<1-2> Operation

<1-2-1> First Mode

In the bed system according to the present embodiment, for example, enabling "automatic driving" with use of the first user interface 4 enables the bed apparatus 1 to be automatically driven. In the following description, automatic driving of the bed apparatus 1 is described. Here, automatic driving (in the present example, also referred to as a "first mode") concerning the time of falling asleep (transitioning from a wakeful state to a sleep state) of the user is described. The user is able to cause the bed apparatus 1 to operate in the first mode by turning "on" automatic driving "during falling asleep" in the screen 42F (FIG. 5(d)) or the screen 42H (FIG. 5(f)) displayed on the first user interface 4.

Figure 6:
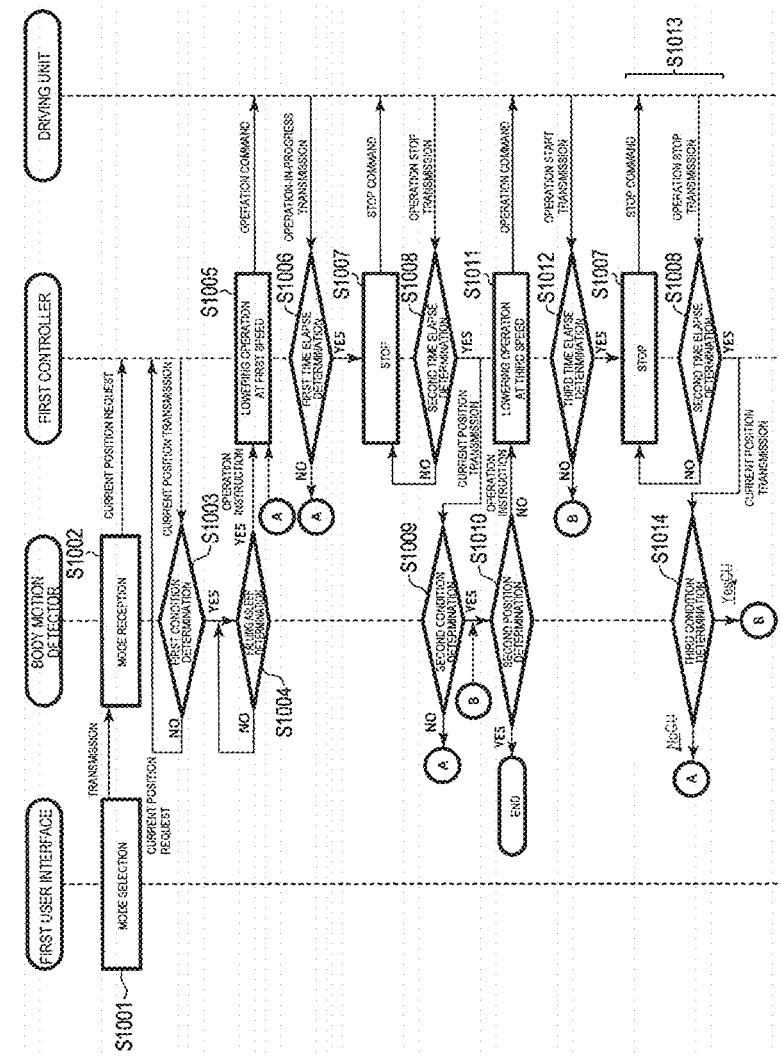
FIG. 6 is a flowchart illustrating an operation in a first mode of the bed system.

The first mode of the bed system according to the present embodiment is described with use of FIG. 6.

[S1001]

When the user selects the "first mode" with use of the first user interface 4, the first user interface 4 transmits that effect as a signal A to the body motion detector 2.

[S1002]

Upon receiving the signal A concerning the "first mode", the body motion detection controller 22 requests current position information about the section from the first controller 101. The first controller 101 transmits the current position information about the section stored in the first memory 106 to the body motion detector 2.

[S1003]

The body motion detection controller 22 determines whether a first condition (for example, "0°< the inclination angle $\theta 1 \leq \alpha 1°$") is satisfied based on the received current position information about the section. When determining that the received current position information does not satisfy the first condition (NO in step S1003), the body motion detection controller 22 requests current position information about the section from the first controller 101.

[S1004]

When determining that the received current position information satisfies the first condition (YES in step S1003), the body motion detection controller 22 determines whether the user has fallen asleep based on the detector 21. The body motion detection controller 22 continues this determination until the user falls asleep. When determining that the user has fallen asleep (YES in step S1004), the body motion detection controller 22 transmits, to the first controller 101, a signal C for performing the "lowering" operation at a first speed. The conceivable "lowering" operation includes "back lowering", "foot lowering", "interlocking lowering", or "height lowering". Moreover, the conceivable "lowering" operation further includes an operation for performing "inclination" from the back section 11 to the lower leg section 14 by making the height of the upper surface of the lower leg section 14 from the floor surface lower than the height of the upper surface of the back section 11 from the floor surface.

[S1005]

Upon receiving the signal C, the first controller 101 refers to information stored in the first memory 106. Then, the first controller 101 transmits a signal B for performing the "lowering" operation at the first speed to the driving unit, and transmits a signal D to the power source unit 102.

[S1006]

The first controller 101 determines, by using the timer 107, whether a first time has elapsed from when step S1005 has been performed. The first controller 101 continues step S1005 until the first time elapses.

[S1007]

When determining that the first time has elapsed (YES in step S1006), the first controller 101 stops the lowering operation of the driving unit. Furthermore, the first controller 101 does not necessarily need to perform stopping but can perform the lowering operation at a second speed (lower than the first speed).

[S1008]

The first controller 101 determines, by using the timer 107, whether a second time has elapsed from when step S1007 has been performed. The first controller 101 continues step S1007 until the second time elapses. When determining that the second time has elapsed (YES in step S1008), the first controller 101 transmits current position information about the section stored in the first memory 106 to the body motion detector 2.

[S1009]

The body motion detector 2 determines whether a second condition (for example, "the inclination angle $\theta 1 \leq \beta 1°$", where $\beta 1 < \alpha 1$) is satisfied based on the current position information about the section. When determining that the received current position information does not satisfy the second condition (NO in step S1009), the body motion detection controller 22 performs step S1005.

[S1010]

When determining that the received current position information satisfies the second condition (YES in step S1009), the body motion detection controller 22 determines whether the section is in a second position (for example, the inclination angle $\theta 1 = 0°$). When determining that the section is in the second position (YES in step S1010), the body motion detection controller 22 ends the first mode. When determining that the section is not in the second position (NO in step S1010), the body motion detection controller 22 transmits a signal C for performing the "lowering" operation at a third speed (which can be almost equal to the first speed, can be lower than or higher than the first speed, and is higher than the second speed) to the first controller 101.

[S1011]

Upon receiving the signal C, the first controller 101 refers to information stored in the first memory 106. Then, the first controller 101 transmits a signal B for performing the "lowering" operation at the third speed to the driving unit, and transmits a signal D to the power source unit 102.

[S1012]

The first controller 101 determines, by using the timer 107, whether a third time has elapsed from when step S1005 has been performed. The first controller 101 repeats step S1010 until the third time elapses.

[S1013]

When determining that the third time has elapsed (YES in step S1012), the first controller 101 repeats step S1007 and step S1008. When determining that the second time has elapsed (YES in step S1008), the first controller 101 transmits the current position information about the section stored in the first memory 106 to the body motion detector 2.

[S1014]

The body motion detector 2 determines whether a third condition (for example, "the inclination angle $\theta 1 \leq \gamma 1°$", where $\gamma 1 < \beta 1$) is satisfied based on the current position information about the section. When determining that the received current position information does not satisfy the third condition (NO in step S1014), the first controller 101 performs step S1005. When determining that the received current position information satisfies the third condition (YES in step S1014), the body motion detection controller 22 performs step S1010.

Furthermore, while, after the lowering operation at the third speed, the "lowering operation at the first speed" is performed, the lowering operation can be performed at "a fourth speed (which can be almost equal to the first speed, can be lower than or higher than the first speed, and is higher than the second speed)".

<1-2-2> Operation Waveforms

Figure 7:
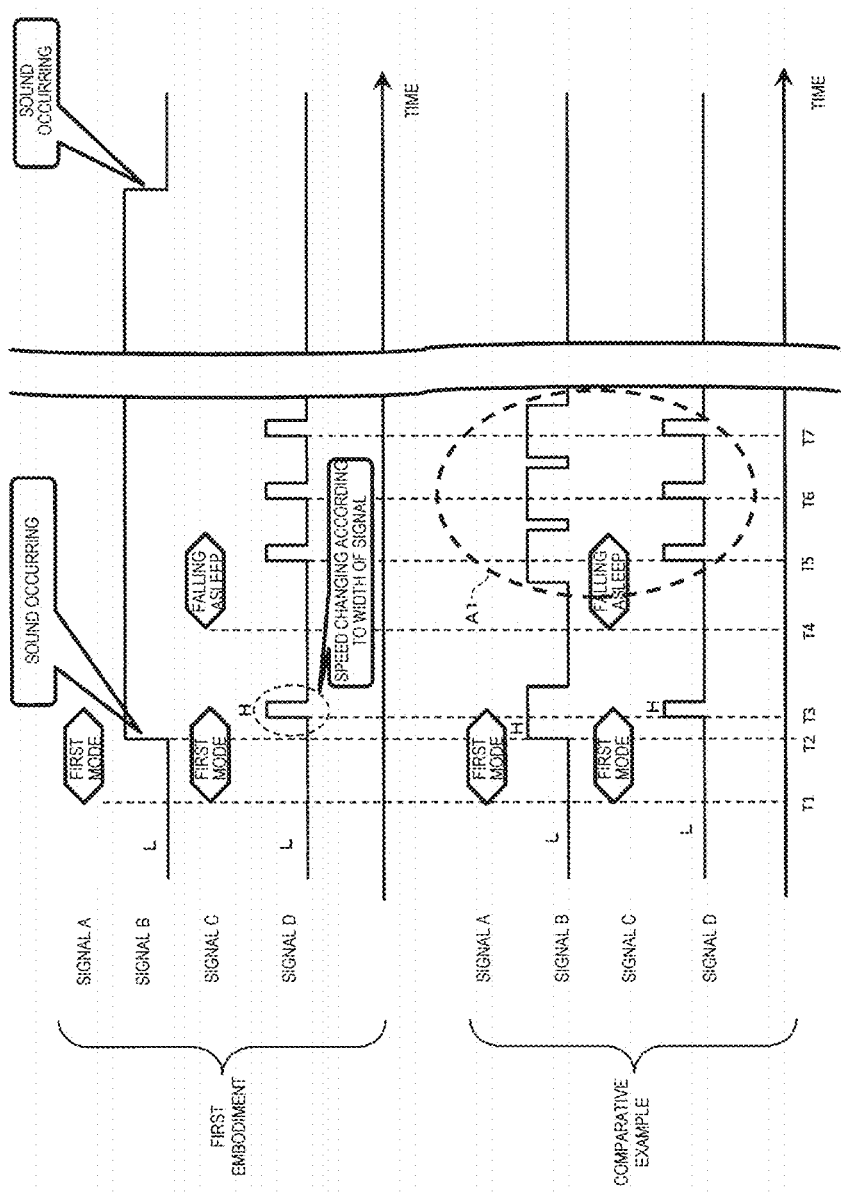
FIG. 7 is a diagram illustrating operation waveforms in the first mode of the bed system and operation waveforms of a bed system serving as a comparative example.

Next, operation waves occurring in the first mode of the bed system according to the present embodiment and operation waves occurring in a bed system according to a comparative example are described with use of FIG. 7.

Here, to facilitate understanding of an operation in the first mode of the bed system according to the first embodiment, the comparative example is also described. The comparative example differs in operation waves from the first embodiment.

As illustrated in FIG. 7, in response to the user selecting the first mode at time T1, a signal A indicating "first mode" is input from the first user interface 4 to the body motion detector 2. This causes the body motion detector 2 to supply a signal C indicating "first mode" to the first controller 101.

At time T2, the first controller 101 generates a signal B of "H" level for setting each section to the "first position", and supplies the signal B of "H" level to each relay circuit. Upon receiving the signal B of "H" level, each relay circuit enters a state of being able to transfer a positive voltage from the power source unit 102 to each driving unit. Then, the first controller 101 supplies a signal D of "H" level to the power source unit 102 at time T3. During a period when the signal D is at "H" level, the power source unit 102 supplies a positive voltage to each relay circuit. Varying the period during which the signal D is at "H" level causes an operation speed of each driving unit to also vary. Specifically, as the period during which the signal D is at "H" level becomes longer, the operation speed of each driving unit becomes higher, and, as the period during which the signal D is at "L" level becomes longer, the operation speed of each driving unit becomes lower.

At time T4, upon receiving a signal C indicating that the user has fallen asleep from the body motion detector 2, the first controller 101 performs steps S1005 to S1014.

Furthermore, while each relay circuit electrically interconnects the power source unit 102 and each driving unit in response to reception of the signal B, a sound with such a magnitude as to reach the user's ears may occur during such interconnection and thus may awake the user after falling asleep. Therefore, the first controller 101 in the first embodiment maintains the signal B of "H" level until the first mode is ended. This causes sounds arising from each relay circuit at the time of selection of the first mode and at the time of ending of the first mode to fall on the user's ears. As illustrated within A1 in FIG. 7, in the comparative example, each driving unit is caused to operate at time, the level of a relay control signal is changed. Therefore, in the comparative example, the number of times of occurrence of sounds arising from each relay circuit becomes large as compared with the first embodiment.

<1-3> Advantageous Effects

The bed system according to the above-described embodiment is configured to automatically drive the bed apparatus 1 based on a signal from the body motion detector 2. Moreover, during automatic driving, the bed apparatus 1 performs a "lowering" operation a plurality of times.

<1-3-1> First Advantageous Effect

First, a first advantageous effect of the first embodiment is described.

During sleep of the user, the position in which, for example, the inclination angle θ1 of the back section 11 is X° (0<X) may be favorable for falling asleep. However, if, in spite of the user being in a sleeping condition, the inclination angle θ1 of the back section 11 is larger than X°, it is hard for the user to turn over in bed.

Therefore, in a case where the user is in a sleeping condition, it is desirable that the inclination angle θ1 of the back section 11 be 0° for ease of turning over in bed.

In the first embodiment, the bed apparatus 1 sets the inclination angle θ1 of the back section 11 to X° until the user falls asleep, and determines falling asleep of the user based on a signal from the body motion detector 2. Then, the bed apparatus 1 sets the inclination angle θ1 of the back section 11 to 0° after the user falls asleep. This enables, while prompting falling asleep of the user, securing the safety of the user after falling asleep.

<1-3-2> Second Advantageous Effect

Next, a second advantageous effect of the first embodiment is described.

In the case of performing back raising, a space (gap) in which, for example, the human body may come is left between the base 10 and the back section 11. In such a space, the body (for example, the arm) of the user or the body of another person (also including, for example, a pet animal) may be present. In such a condition, there is no problem unless back lowering is performed. However, in such a case, if back lowering is automatically performed, the body of the user or the body of another person may be wedged between the base 10 and the back section 11 and thus may get injured.

In the first embodiment, while the "lowering" operation of sections is automatically performed after the user has fallen asleep, on the way (at the second position), the "lowering" operation is performed at low speed or is stopped for a given period of time. With this operation, even in a case where the body of the user or the body of another person is wedged between the base 10 and the back section 11, the back section 11 is stopped before the body gets injured. In this way, causing the bed apparatus 1 to perform an operation in stages enables improving safety.

<1-3-3> Third Advantageous Effect

Next, a third advantageous effect of the first embodiment is described.

As mentioned above, while each relay circuit electrically interconnects the power source unit 102 and each driving unit, a sound with such a magnitude as to reach the user's ears may occur during such interconnection. In consideration of an influence on sleep of the user, it is desirable to perform the lowering operation as quietly as possible (for example, with respect to sound or vibration). For example, in the comparative example illustrated in FIG. 7, a sound arising from the relay circuit occurs each time the driving unit is driven.

However, according to the above-described embodiment, in automatic driving, a sound arising from the relay circuit occurs only a bare minimum number of times. Therefore, it is possible to keep the influence on sleep of the user during sleep to a bare minimum.

As described above, in the bed system according to the above-described embodiment, detecting the condition (for example, sleep or awakening) of the user enables prompting falling asleep, securing safety, and keeping the influence on sleep to a bare minimum. As a result, it is possible to provide a high-quality bed system.

<1-4> Modification Example 1

The first speed, the second speed, the second position, or the first time in the above-described flow illustrated in FIG.

6 can be determined based on the degree of relaxation of the user. The degree of relaxation of the user can be measured by, for example, the body motion detector 2. The first controller 101 determines the first speed, the second speed, the second position, and the first time based on the degree of relaxation of the user. The bed system can perform the first mode in this way.

<1-5> Modification Example 2

The first speed, the second speed, the second position, or the first time in the above-described flow illustrated in FIG. 6 can be determined based the depth of sleep (sleeping condition) of the user. The sleeping condition of the user is measured by, for example, the body motion detector 2. The first controller 101 determines the first speed, the second speed, the second position, and the first time based on the sleeping condition of the user. The bed system can perform the first mode in this way.

<1-6> Modification Example 3

Figure 8:
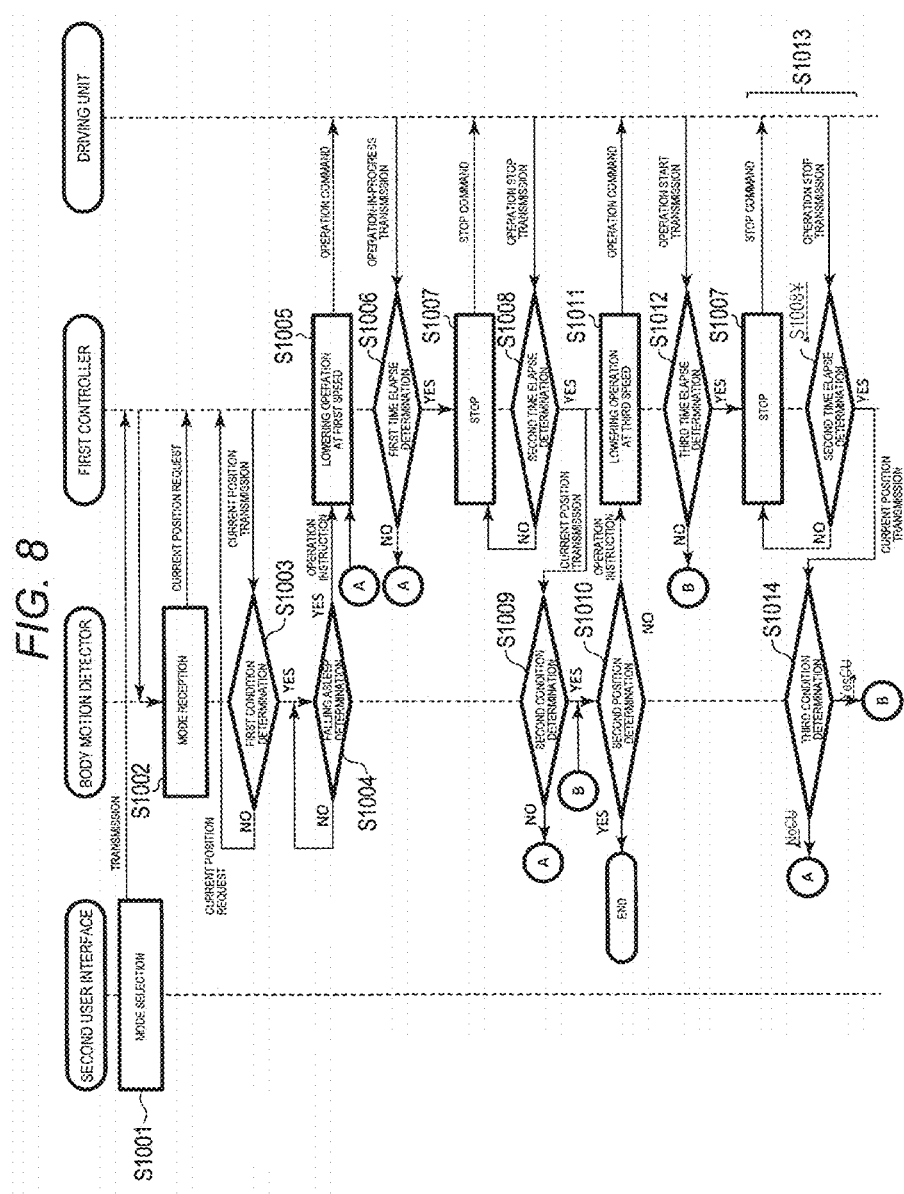
FIG. 8 is a flowchart illustrating an operation of a modification example in the first mode of the bed system.

While, here, the bed system being controlled via the first user interface 4 has been described, the bed system can be controlled via the second user interface 5. As illustrated in FIG. 8, the second user interface 5 transmits an instruction directed to the bed system as a signal A to the first controller 101. Upon receiving the signal A from the second user interface 5, the first controller 101 forwards the signal A to the body motion detector 2. This enables performing the same operation as that in the flow illustrated in FIG. 6.

When, without using automatic driving, the user manually performs the "lowering operation" (or the "raising operation") via the first user interface 4 or the second user interface 5, the speed at which to perform the lowering operation of the bed can be set higher than each of all of the first speed, the second speed, the third speed, and the fourth speed. As a result, the present invention attains the first advantageous effect and the second advantageous effect.

<2> Second Embodiment

A second embodiment is described. In the first embodiment, automatic driving for prompting falling asleep has been described. In the second embodiment, automatic driving for prompting awakening (sit-up) is described. Furthermore, the basic configuration and basic operation of the bed system according to the second embodiment are similar to those of the bed system according to the above-described first embodiment. Accordingly, descriptions about particulars described in the above-described first embodiment and particulars which are able to be easily analogized from the above-described first embodiment are omitted here.

<2-1> Second Mode

Figure 9:
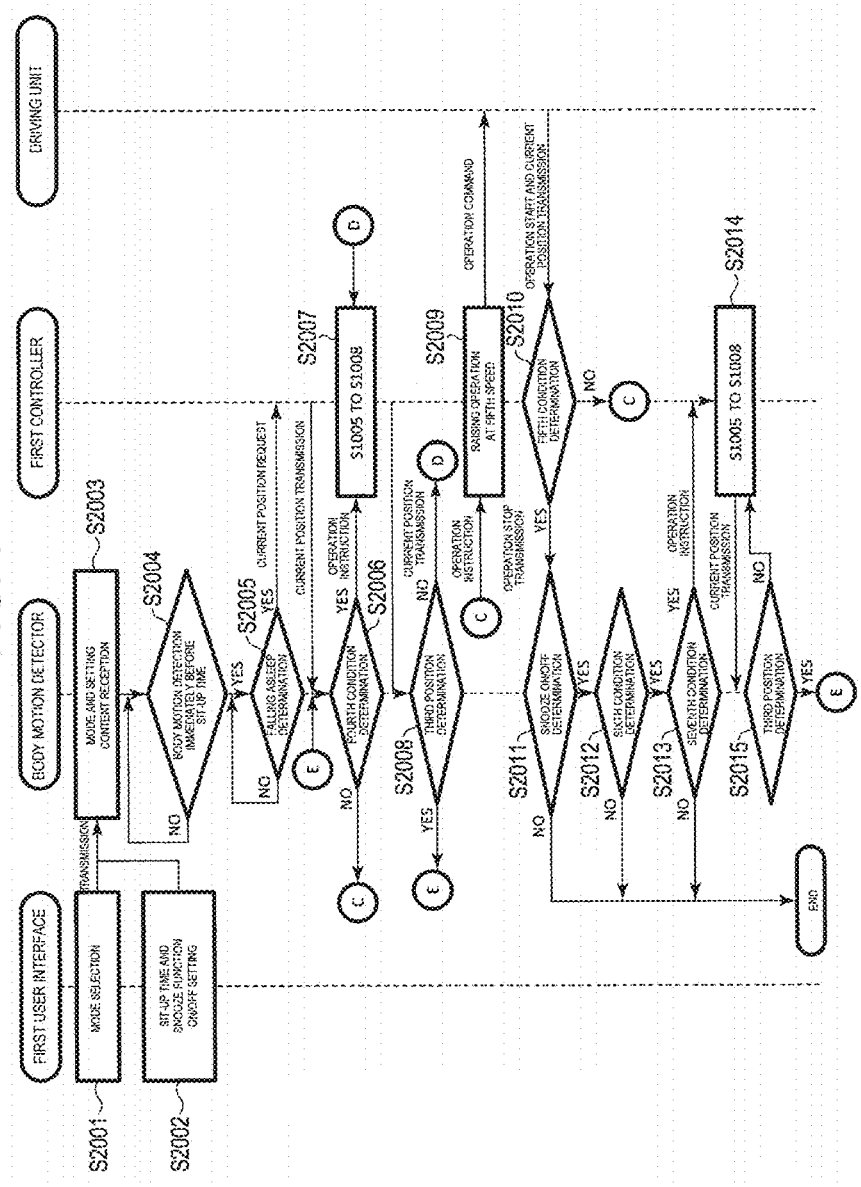
FIG. 9 is a flowchart illustrating an operation in a second mode of the bed system.

A second mode in the bed system according to the present embodiment is described with use of FIG. 9. The second mode is a mode for awakening the user by raising the back section when the sleep of the user is shallow (there is a body motion) in the vicinity of the sit-up scheduled time set by the user (the time at which the user intends to sit up).
[S2001] and [S2002]

The user selects the second mode via the first user interface 4, and sets the sit-up scheduled time and ON or OFF of the snooze function. Specifically, the user sets the sit-up scheduled time and ON or OFF of the snooze function to the bed apparatus 1 with use of, for example, the first user interface 4.

[S2003]

Upon receiving a signal A concerning the second mode, the sit-up scheduled time, and ON or OFF of the snooze function, the body motion detector 2 stores information concerning the sit-up scheduled time and ON or OFF of the snooze function in the second memory 23.

[S2004]

The body motion detector 2 determines whether the detector 21 has detected, for example, the body motion, heartbeat, and respiration of the user in the vicinity of (immediately before) the sit-up scheduled time stored in the second memory 23. The conceivable example of the vicinity of the sit-up scheduled time includes 30 minutes before the sit-up scheduled time. However, the vicinity of the sit-up scheduled time is not limited to this. For example, in a case where the user sets "6 a.m.", the body motion detector 2 determines whether the body motion has been detected at "5 a.m. to 6 a.m.".

[S2005]

When determining that the body motion has been detected in the vicinity of the sit-up scheduled time (YES in step S2004), the body motion detection controller 22 determines whether the user is in a sleeping condition based on the detector 21. The body motion detection controller 22 repeats this determination until the user falls asleep. When determining that the user has fallen asleep (YES in step S2005), the body motion detection controller 22 requests the current position information about the section from the first controller 101. The first controller 101 supplies the current position information about the section stored in the first memory 106 to the body motion detector 2 in response to the request.

[S2006]

The body motion detection controller 22 determines whether a fourth condition (for example, "0°< the inclination angle θ1") is satisfied based on the received current position information about the section.

[S2007]

When the body motion detection controller 22 determines that the received current position information satisfies the fourth condition (YES in step S2006), the bed system performs steps S1005 to S1008.

[S2008]

After step S2007 is performed, the body motion detector 2 determines whether the section is in a third position (for example, the inclination angle θ1=0°) based on the current position information about the section supplied from the first controller 101. When determining that the section is in the third position (YES in step S2008), the body motion detector 2 repeats step S2006. When determining that the section is not in the third position (NO in step S2008), the first controller 101 repeats step S2007.

[S2009]

When determining that the received current position information does not satisfy the fourth condition (NO in step S2006), the body motion detection controller 22 transmits a signal C for performing the raising operation at a fifth speed (which can be almost equal to the first speed, can be lower than or higher than the first speed, and is higher than the second speed) to the first controller 101. Upon receiving the signal C, the first controller 101 accesses the first memory 106 and controls the driving unit to perform the raising operation at the fifth speed.

Furthermore, the fifth speed is able to be changed as appropriate each time step S2009 is repeated. Moreover, while, in the description here, the raising operation is assumed to be the back raising operation, the present embodiment is not limited to this, and the upper leg raising operation or the height raising operation can be performed simultaneously.

[S2010]

The first controller 101 determines whether a fifth condition (for example, the inclination angle θ1=α2°) is satisfied. When determining that the fifth condition is not satisfied (NO in step S2010), the first controller 101 repeats step S2009.

[S2011]

When determining that the fifth condition is satisfied (YES in step S2010), the first controller 101 transmits that effect to the body motion detector 2, so that the body motion detector 2 determines ON or OFF of snooze.

When determining that snooze is OFF (NO in step S2011), the body motion detector 2 ends the second mode.

[S2012]

When determining that snooze is ON (YES in step S2011), the body motion detector 2 determines whether a sixth condition (for example, the user being sleeping) is satisfied.

When determining that the sixth condition is not satisfied (NO in step S2012), the body motion detector 2 ends the second mode.

[S2013] When determining that the sixth condition is satisfied (YES in step S2012), the body motion detector 2 determines whether a seventh condition (for example, the number of times of snooze or the number of times of reciprocating back raising or back lowering operations being less than or equal to a predetermined value) is satisfied.

When determining that the seventh condition is not satisfied (NO in step S2013), the body motion detector 2 ends the second mode.

[S2014]

When the body motion detector 2 determines that the seventh condition is satisfied (YES in step S2013), the bed system performs steps S1005 to S1008.

[S2015] The body motion detector 2 determines whether the section is in a third position (for example, the inclination angle θ1=0°) based on the position information about the section supplied from the first controller 101. When determining that the section is in the third position (YES in step S2015), the body motion detector 2 repeats step S2006. When determining that the section is not in the third position (NO in step S2015), the first controller 101 repeats step S2014.

Furthermore, in a case where, after a given period of time has elapsed from ending of the second mode, falling asleep of the user has been confirmed again by the body motion detector 2, "steps S2005 to S2015" are repeated.

Furthermore, operation waves in the second mode are similar to the operation waves in the first mode and are, therefore, omitted from description here. Furthermore, in the second mode related to "sit-up", waveforms similar to those in the comparative example described in <1-2-2> can be employed.

<2-2> Advantageous Effects in Second Mode

To prompt awakening of the user, the "raising" operation or the "lowering" operation may be favorable. Particularly, performing the "raising" operation or the "lowering" operation in a case where sleeping of the user is shallow (there is a body motion) enables prompting wakening of the user. Particularly, alternately repeating the "raising" operation and the "lowering" operation enables prompting wakening of the user. In the second mode, when the body motion of the user is detected in the vicinity of the sit-up scheduled time of the user, the "raising" operation or the "lowering" operation is performed. As a result, it is possible to prompt awakening of the user at the sit-up scheduled time of the user.

Moreover, in the second embodiment, with respect to portions similar to those in the first embodiment, similar advantageous effects are able to be obtained.

<3> Third Embodiment

A third embodiment is described. In the first embodiment, automatic driving for prompting falling asleep has been described. In the third embodiment, automatic driving for steadying down, for example, respiration of the user is described. Furthermore, the basic configuration and basic operation of the bed system according to the third embodiment are similar to those of the bed system according to the above-described first embodiment. Accordingly, descriptions about particulars described in the above-described first embodiment and particulars which are able to be easily analogized from the above-described first embodiment are omitted here.

<3-1> Third Mode

Figure 10:
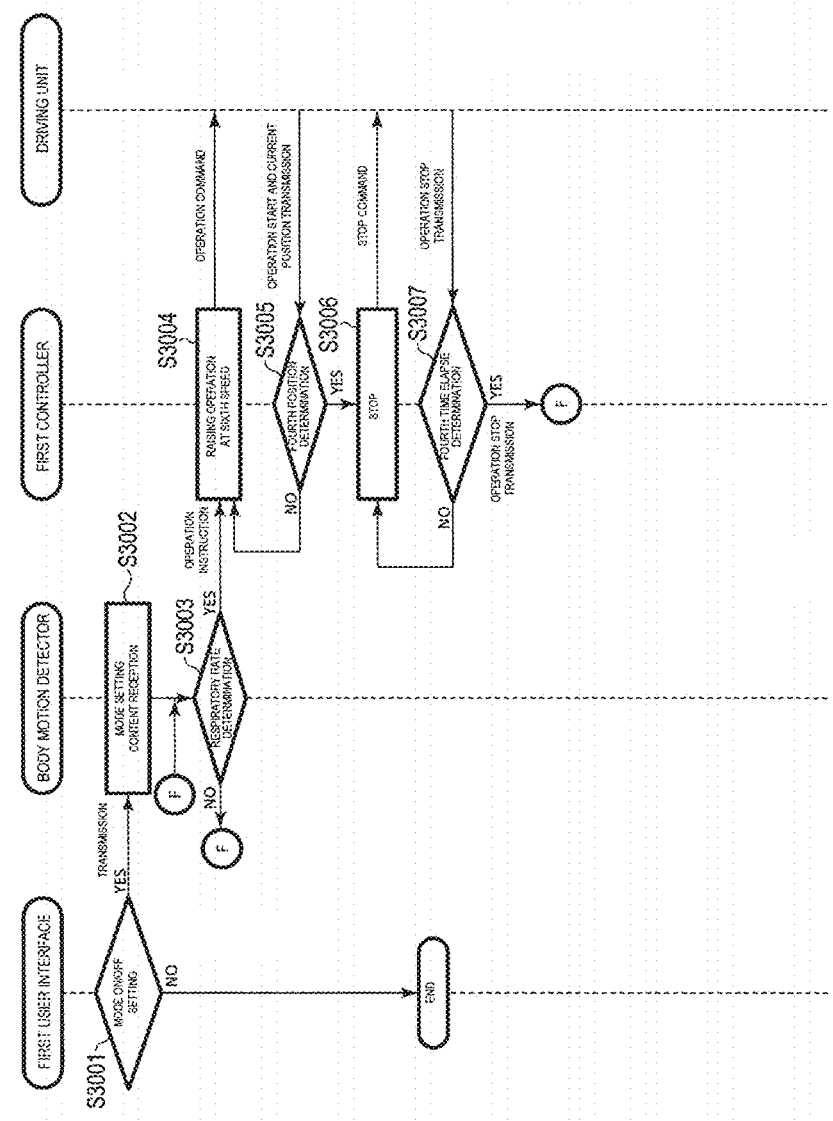
FIG. 10 is a flowchart illustrating an operation in a third mode of the bed system.

A third mode in the bed system according to the present embodiment is described with use of FIG. 10. The third mode is a mode which is used when the user's respiration has become unsteady during sleep.

Making the inclination angle of the back section larger than 0° causes the user's diaphragm to move down and thus facilitates maintaining the user's airway for easier breathing. Therefore, in the third mode, when the user's respiration has become unsteady (for example, in a case where the user gets hyperventilation), the bed system performs the "raising" operation, checks the state of hyperventilation after the elapse of a given period of time, and determines whether to further perform the "raising" operation.

[S3001]

The first user interface 4 determines ON or OFF of the third mode. When determining that the third mode is OFF (NO in step S3001), the first user interface 4 ends the operation.

When determining that the third mode is ON (YES in step S3001), the first user interface 4 transmits that effect as a signal A to the body motion detector 2.

[S3002] and [S3003]

Upon receiving the signal A concerning the "third mode", the body motion detection controller 22 detects the respiratory rate of the user with the detector 21, and determines whether the respiratory rate satisfies a first value (for example, α3 times per minute). When determining that the respiratory rate is less than the first value (NO in step S3003), the body motion detection controller 22 repeats step S3003.

Without being limited to this case, for example, upon receiving the signal A concerning the "third mode", the body motion detection controller 22 can detect a variation in the respiratory rate of the user with the detector 21. Specifically, when the variation exceeds a given threshold value, the body motion detection controller 22 can advance the operation to step S3004, and, when the variation does not exceed the given threshold value, the body motion detection controller 22 can repeat step S3003.

[S3004] When determining that the respiratory rate is greater than or equal to the first value (YES in step S3003), the body motion detection controller 22 transmits a signal C for performing the "raising" operation at a sixth speed. Furthermore, the sixth speed is able to be changed as appropriate each time step S3004 is repeated.

Upon receiving the signal C, the first controller 101 refers to information stored in the first memory 106. Then, the first controller 101 transmits a signal B for performing the "raising" operation at the sixth speed to the driving unit, and transmits a signal D to the power source unit 102.

[S3005]

The body motion detection controller 22 determines whether the section is in a fourth position (for example, the inclination angle $\theta 1 = \beta 3°$). When determining that the section is not in the fourth position (NO in step S3005), the body motion detection controller 22 repeats step S3004.

[S3006]

When determining that the section is in the fourth position (YES in step S3005), the first controller 101 stops the raising operation of the driving unit. Furthermore, the first controller 101 does not necessarily need to perform stopping but can perform the raising operation at a second speed lower than the sixth speed.

[S3007]

The first controller 101 determines whether a fourth time has elapsed from step S3006. When determining that the fourth time has not yet elapsed (NO in step S3007), the first controller 101 repeats step S3006. When determining that the fourth time has elapsed (YES in step S3007), the first controller 101 repeats step S3003.

Furthermore, a determination as to "whether the section is in the fourth position" and a determination as to "whether the fourth time has elapsed" can be simultaneously performed as determinations in steps S3005 and S3007.

<3-2> Advantageous Effects in Third Mode

In the third mode, even in a case where an abnormal change has occurred in respiration of the user, automatic driving is able to be performed in such a way as to make the user easily respire.

Moreover, in the third embodiment, with respect to portions similar to those in the first and second embodiments, similar advantageous effects are able to be obtained.

<3-3> Fourth Mode

Figure 11:
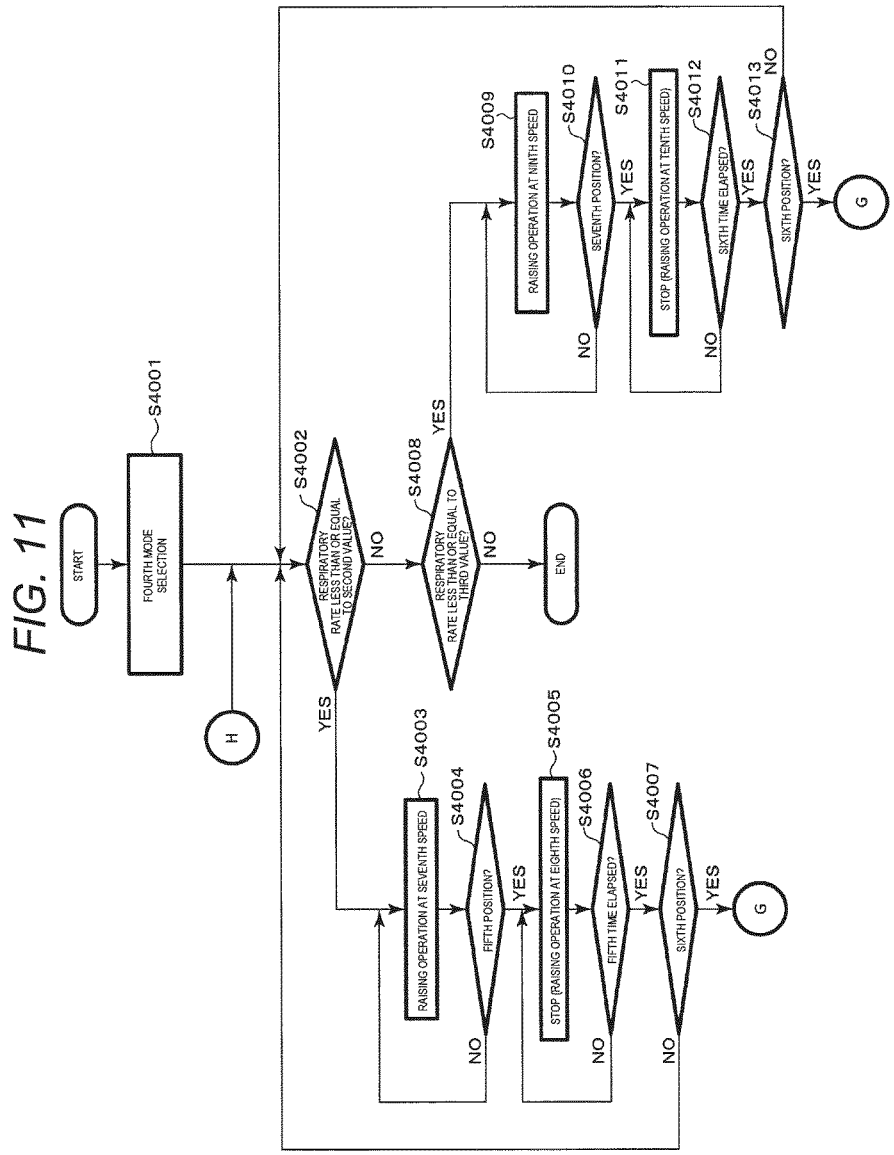
FIG. 11 is a flowchart illustrating an operation in a fourth mode of the bed system.
Figure 12:
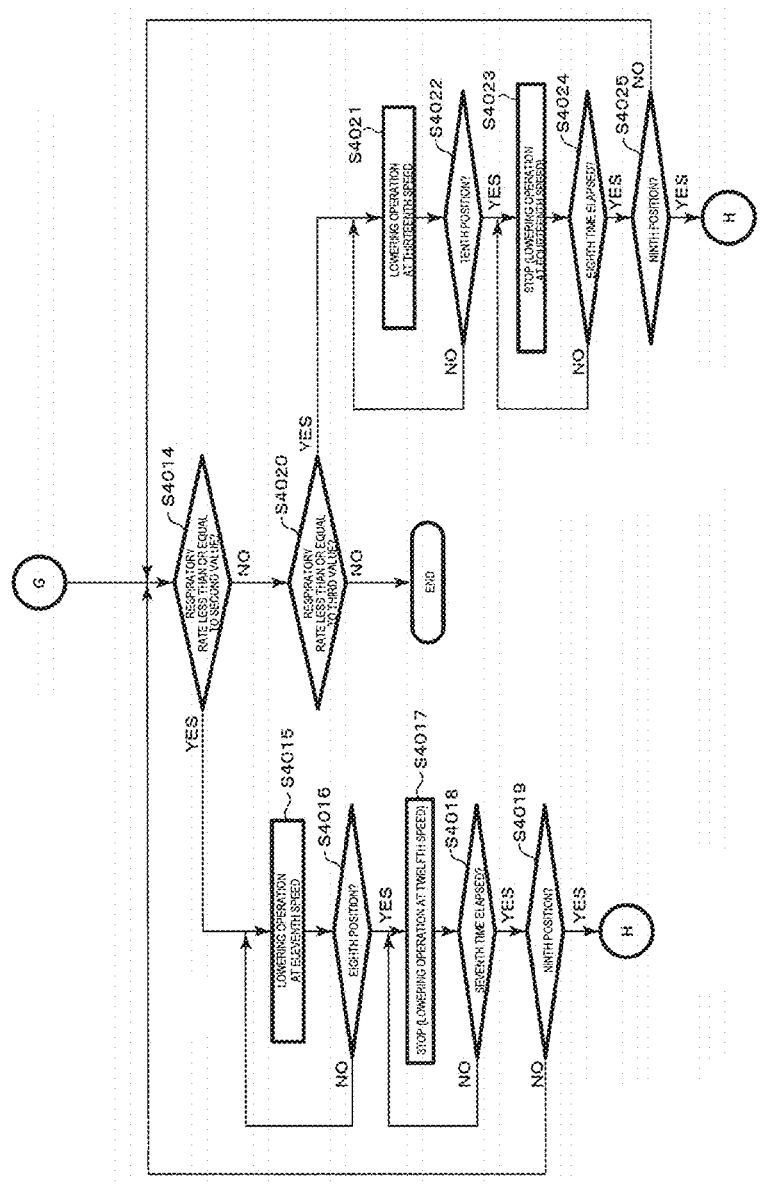
FIG. 12 is a flowchart illustrating an operation in the fourth mode of the bed system.

A fourth mode in the bed system according to the present embodiment is described with use of FIG. 11 and FIG. 12. The fourth mode is a mode which is used when a respiratory disorder such as apnea or snoring has occurred during sleep of the user.

The fourth mode is a mode which, when the user's respiration has become unsteady, determines whether the symptom is severe or mild, and performs different control operations between when the symptom is severe and when the symptom is mild.

[S4001]

In response to the user selecting the "fourth mode" via the first user interface 4, the first controller 101 controls the bed apparatus 1 to operate in the "fourth mode".

[S4002]

The body motion detector 2 determines whether the respiratory rate of the user is less than or equal to a second value (for example, $\alpha 4$ times per minute). If the respiratory rate is less than or equal to the second value (YES in step S4002), it is determinable that the respiratory disorder of the user is severe.

[S4003]

When determining that the respiratory rate of the user is less than or equal to the second value (YES in step S4002), the body motion detector 2 causes the bed apparatus 1 to perform the "raising" operation at a seventh speed. This seventh speed is, for example, higher than a ninth speed described below.

[S4004]

The body motion detector 2 determines whether the section has reached a fifth position (for example, the inclination angle $\theta 1 = \beta 4°$). The first controller 101 repeats step S4003 until each section reaches the fifth position. Furthermore, the fifth position can be updated each time steps S4003 to S4007 are repeated.

[S4005]

When determining that each section has reached the fifth position (YES in step S4004), the first controller 101 stops the raising operation. Furthermore, the first controller 101 can perform the "raising" operation at an eighth speed lower than the seventh speed.

[S4006]

The body motion detector 2 determines whether a fifth time has elapsed from the start time of step S4005. When determining that the fifth time has not yet elapsed from the start time of step S4005 (NO in step S4006), the first controller 101 repeats step S4005.

[S4007]

When determining that the fifth time has elapsed from the start time of step S4005 (YES in step S4006), the body motion detector 2 determines whether the section has reached a sixth position (for example, the inclination angle $\theta 1 = \gamma 4°$, where $\gamma 4 > \beta 4$). When determining that the section has not yet reached the sixth position (NO in step S4007), the first controller 101 repeats step S4002.

[S4008]

When determining that the respiratory rate of the user is neither less than nor equal to the second value (NO in step S4002), the body motion detector 2 determines whether the respiratory rate of the user is less than or equal to a third value (for example, $\omega 4$ times per minute, where $\omega 4 > \alpha 4$). If the respiratory rate is less than or equal to the third value (YES in step S4008), it is determinable that the respiratory disorder of the user is mild.

[S4009]

When determining that the respiratory rate of the user is less than or equal to the third value (YES in step S4008), the first controller 101 performs the "raising" operation at a ninth speed. This ninth speed can be lower than, for example, the seventh speed. In this way, in the fourth mode, in the case of the respiratory disorder of the user being severe, the "raising" operation is performed at high speed, and, in the case of the respiratory disorder of the user being mild, the "raising" operation is performed at low speed.

[S4010]

The body motion detector 2 determines whether the section has reached a seventh position (for example, the inclination angle $\theta 1 = \delta 4°$, where $\delta 4 < \beta 4$). The body motion detector 2 repeats step S4009 until the section reaches the seventh position. This seventh position can be a position lower (smaller in inclination angle) than, for example, the fifth position. Furthermore, the seventh position can be updated each time steps S4009 to S4013 are performed.

[S4011]

When determining that each section has reached the seventh position (YES in S4010), the first controller 101 stops the raising operation. Furthermore, the first controller 101 can perform the "raising" operation at a tenth speed lower than the ninth speed.

[S4012]

The body motion detector 2 determines whether a sixth time has elapsed from the start time of step S4011. When determining that the sixth time has not yet elapsed from the start time of step S4011 (NO in step S4012), the first controller 101 repeats step S4011.

[S4013]

When determining that the sixth time has elapsed from the start time of step S4011 (YES in step S4012), the body motion detector 2 determines whether the section has reached the sixth position. When determining that the section has not yet reached the sixth position (NO in step S4013), the body motion detector 2 repeats step S4002.

[S4014]

The continuation from each of steps S4007 and S4013 is described with use of FIG. 12.

If the section has reached the sixth position (YES in each of steps S4007 and S4013), the body motion detector 2 determines whether the respiratory rate of the user is less than or equal to the second value.

[S4015]

When determining that the respiratory rate of the user is less than or equal to the second value (YES in step S4014), the first controller 101 performs the "lowering" operation at an eleventh speed. This eleventh speed is higher than, for example, a thirteenth speed described below.

[S4016]

The body motion detector 2 determines whether the section has reached an eighth position. The first controller 101 repeats step S4015 until the section reaches the eighth position. Furthermore, each time steps S4015 to S4018 are repeated, the eighth position is updated to a lower position (a smaller inclination angle).

[S4017]

When determining that the section has reached the eighth position (YES in step S4016), the first controller 101 stops the lowering operation. Furthermore, the first controller 101 can perform the "lowering" operation at a twelfth speed lower than the eleventh speed.

[S4018]

The body motion detector 2 determines whether a seventh time has elapsed from the start time of step S4017. When determining that the seventh time has not yet elapsed from the start time of step S4017 (NO in step S4018), the first controller 101 repeats step S4017.

[S4019]

When determining that the seventh time has elapsed from the start time of step S4017 (YES in step S4018), the body motion detector 2 determines whether the section has reached a ninth position. When determining that the section has not yet reached the ninth position (NO in step S4019), the body motion detector 2 repeats step S4014. When determining that the section has reached the ninth position (YES in step S4019), the body motion detector 2 repeats step S4002. When determining that the section has not yet reached the ninth position (NO in step S4019), the body motion detector 2 repeats step S4014.

[S4020]

When determining that the respiratory rate of the user is neither less than nor equal to the second value (NO in step S4014), the body motion detector 2 determines whether the respiratory rate of the user is less than or equal to a third value.

[S4021]

When determining that the respiratory rate of the user is less than or equal to the third value (YES in step S4020), first controller 101 performs the "lowering" operation at a thirteenth speed. This thirteenth speed can be lower than, for example, the eleventh speed. In this way, in the fourth mode, in the case of the respiratory disorder of the user being severe, the "lowering" operation is performed at high speed, and, in the case of the respiratory disorder of the user being mild, the "lowering" operation is performed at low speed.

[S4022]

The body motion detector 2 determines whether the section has reached a tenth position (for example, the inclination angle $\theta 1 = \varepsilon 4°$, where $\beta 4 < \varepsilon 4 < \gamma 4$). The first controller 101 repeats step S4021 until the section reaches the tenth position. This tenth position can be a position higher (larger in inclination angle) than, for example, the eighth position. Furthermore, each time steps S4021 to S4024 are repeated, the tenth position can be uploaded.

[S4023]

When determining that the section has reached the tenth position (YES in step S4022), the first controller 101 stops the lowering operation. Furthermore, the first controller 101 can perform the "lowering" operation at a fourteenth speed lower than the thirteenth speed. Furthermore, the fourteenth speed is able to be changed as appropriate each time step S4023 is repeated.

[S4024]

The body motion detector 2 determines whether an eighth time has elapsed from the start time of step S4023. When determining that the eighth time has not yet elapsed from the start time of step S4023 (NO in step S4024), the first controller 101 repeats step S4023.

[S4025]

When determining that the eighth time has elapsed from the start time of step S4023 (YES in step S4024), the body motion detector 2 determines whether the section has reached the ninth position. When determining that the section has not yet reached the ninth position (NO in step S4025), the body motion detector 2 repeats step S4014. When determining that the section has reached the ninth position (YES in step S4025), the body motion detector 2 repeats step S4002.

Furthermore, the bed system can end the fourth mode after a predetermined time (a time stored in the first memory 106 or the second memory 23 or a time supplied from the first user interface 4) elapses from the time of performing the fourth mode.

<3-6> Advantageous Effects in Fourth Mode

As described above, in the fourth mode, even in a case where an abnormal change has occurred in respiration of the user, automatic driving is able to be performed more finely than in the other modes in such a way as to make the user easily respire.

Moreover, in the third embodiment, with respect to portions similar to those in the first and second embodiments, similar advantageous effects are able to be obtained.

<4> Fourth Embodiment

A fourth embodiment is described. In the first embodiment, automatic driving for prompting falling asleep has been described. In the fourth embodiment, a method of safely performing automatic driving is described. Furthermore, the basic configuration and basic operation of the bed system according to the fourth embodiment are similar to those of the bed system according to the above-described first embodiment. Accordingly, descriptions about particulars described in the above-described first embodiment and particulars which are able to be easily analogized from the above-described first embodiment are omitted here.

<4-1> Fifth Mode

Figure 13:
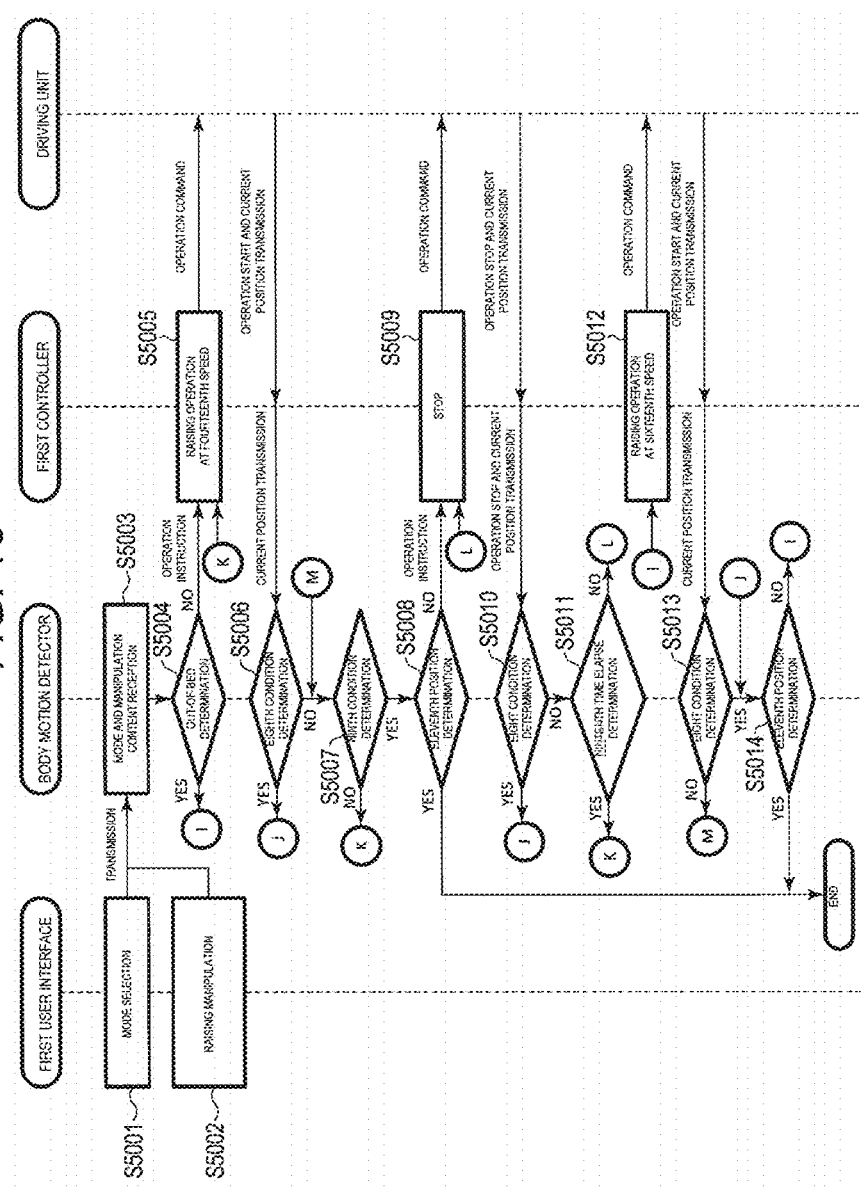
FIG. 13 is a flowchart illustrating an operation in a fifth mode of the bed system.

A fifth mode in the bed system according to the present embodiment is described with use of FIG. 13. The fifth mode is a mode which is used when the user safely performs automatic driving. Specifically, the fifth mode is a mode for performing an operation at a lower speed when the user P is lying in bed than when the user is out of bed.

[S5001] and [S5002]

The user selects the fifth mode via the first user interface 4, and performs a raising manipulation.

[S5003]

The body motion detector 2 receives the fifth mode and a signal A concerning the "raising" manipulation.

[S5004]

The body motion detector 2 determines whether the user is out of bed.

[S5005]

When determining that the user is not out of bed (NO in step S5004), the body motion detector 2 transmits a signal C for performing the "raising" operation at a fourteenth speed to the first controller 101. The first controller 101 performs the "raising" operation at the fourteenth speed based on the signal C. Furthermore, the fourteenth speed is able to be changed as appropriate each time step S5005 is repeated.

[S5006]

The body motion detector 2 receives current position information about the section from the first controller 101.

Upon this reception, the body motion detector 2 determines whether an eighth condition (for example, "the user being out of bed" or "no condition") is satisfied.

[S5007]

When determining that the eighth condition is not satisfied (NO in step S5006), the body motion detector 2 determines whether a ninth condition (for example, "the inclination angle θ1 being less than or equal to α5°" or "β5 seconds having elapsed from step S5005") is satisfied. When the body motion detector 2 determines that the ninth condition is not satisfied (NO in step S5007), the first controller 101 performs step S5005.

[S5008]

When determining that the ninth condition is satisfied (YES in step S5007), the body motion detector 2 determines whether the section is in an eleventh position (for example, the inclination angle θ1=γ5°, where α5<γ5). When determining that the section is in the eleventh position, the body motion detector 2 ends the operation.

[S5009]

When determining that the section is not in the eleventh position, the body motion detector 2 transmits a signal C for stopping the raising operation. The first controller 101 stops the raising operation based on the signal C. Furthermore, the first controller 101 can perform the "raising" operation at a fifteenth speed lower than the fourteenth speed.

[S5010]

The body motion detector 2 receives current position information about the section from the first controller 101.

Upon this reception, the body motion detector 2 determines whether an eighth condition (for example, "the user being out of bed" or "no condition") is satisfied.

[S5011]

When determining that the eighth condition is not satisfied (NO in step S5010), the body motion detector 2 determines whether a ninth time has elapsed from step S5009. When the body motion detector 2 determines that the ninth time has elapsed (YES in step S5011), the first controller 101 performs step S5005. When the body motion detector 2 determines that the ninth time has not yet elapsed (NO in step S5011), the first controller 101 performs step S5009.

[S5012]

When determining that the user is out of bed (YES in step S5004), the body motion detector 2 transmits a signal C for performing the "raising" operation at a sixteenth speed (which can be almost equal to the fourteenth speed, can be lower or higher than the fourteenth speed, and is higher than the fifteenth speed) to the first controller 101. The first controller 101 performs the "raising" operation at the sixteenth speed based on the signal C. Furthermore, the sixteenth speed is able to be changed as appropriate each time step S5012 is repeated.

[S5013]

The body motion detector 2 receives current position information about the section from the first controller 101.

Upon this reception, the body motion detector 2 determines whether the eighth condition is satisfied.

When determining that the eighth condition is not satisfied (NO in step S5013), the body motion detector 2 repeats step S5007.

[S5014]

When determining that the eighth condition is satisfied (YES in each of steps S5006, S5010, and S5013), the body motion detector 2 determines whether the section is in the eleventh position. When determining that the section is in the eleventh position (YES in step S5014), the body motion detector 2 ends the operation. When the body motion detector 2 determines that the section is not in the eleventh position (NO in step S5014), the first controller 101 repeats step S5012.

<4-2> Advantageous Effects in Fifth Mode

As described above, in the fifth mode, since lying-in-bed and out-of-bed of the user are monitored finely, it is possible to cause the bed apparatus to operate more safely.

Furthermore, while, in the fifth mode, the body motion detector 2 detects lying-in-bed and out-of-bed of the user, the present embodiment is not limited to this. The body motion detector 2 can detect body motion of the user and use, instead of information about lying-in-bed and out-of-bed, information about the detected body motion. Moreover, while, in the fifth mode, only the "raising" operation has been described in a limited manner, the present embodiment is also applicable to the "lowering" operation (a sixth mode). In that case, the ninth condition becomes a condition such as "the inclination angle θ1 being less than or equal to ω5°" or "ε5 seconds having elapsed from step S5005", and the eleventh position becomes, for example, "the inclination angle θ1=0°".

Moreover, in the fourth embodiment, with respect to portions similar to those in the first and second embodiments, similar advantageous effects are able to be obtained.

<5> Fifth Embodiment

A fifth embodiment is described. In the first embodiment, automatic driving for prompting falling asleep has been described. In the fifth embodiment, a method capable of preventing aspiration after eating and capable of appropriately coping with a case where there is a presage of abnormality in heartbeat or respiratory status is described. Furthermore, the basic configuration and basic operation of the bed system according to the fifth embodiment are similar to those of the bed system according to the above-described first embodiment. Accordingly, descriptions about particulars described in the above-described first embodiment and particulars which are able to be easily analogized from the above-described first embodiment are omitted here.

<5-1> Seventh Mode

Figure 14:
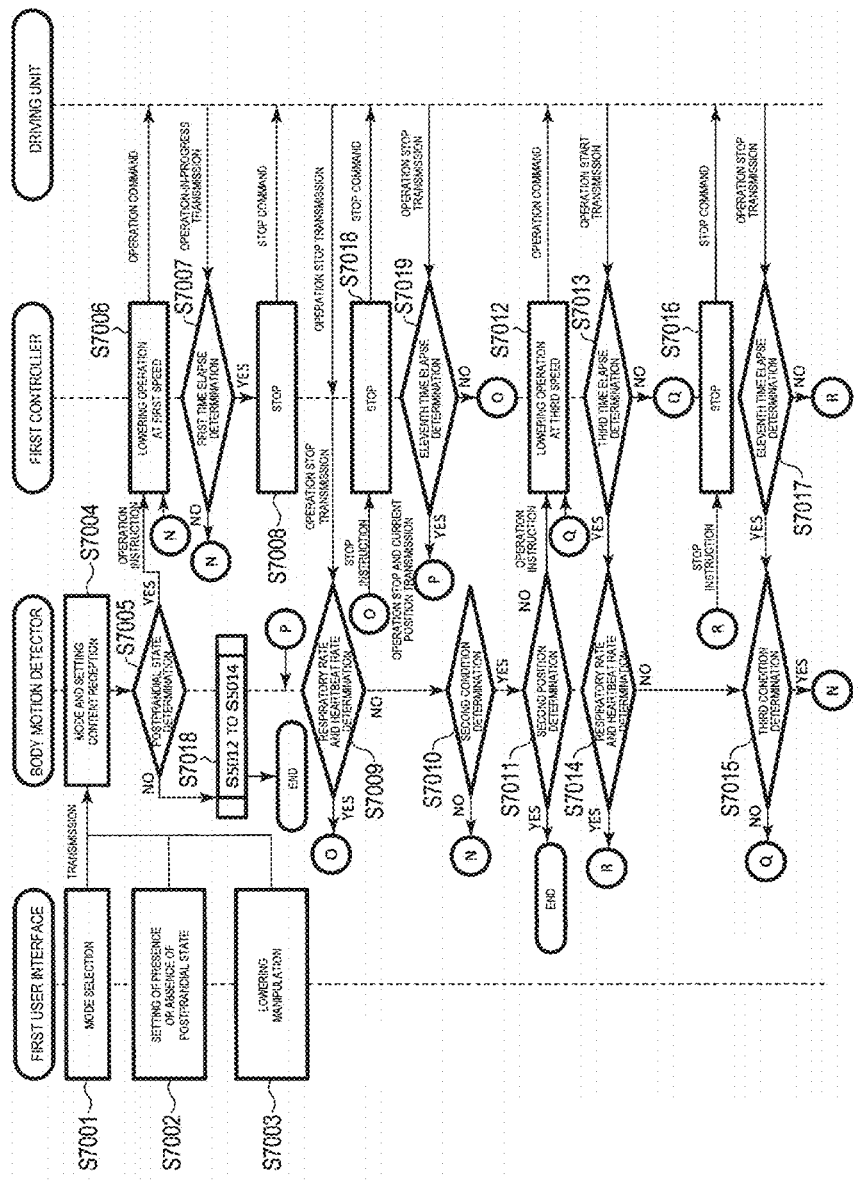
FIG. 14 is a flowchart illustrating an operation in a seventh mode of the bed system.

A seventh mode in the bed system according to the present embodiment is described with use of FIG. 14. The seventh mode is a mode which is used when automatic driving configured in consideration of preventing aspiration after eating is performed.

In a case after the user eats, it is desirable that the back be kept raised for a given period of time after eating and the "lowering" operation be gradually performed at low speed. On the other hand, in the case of gradually performing the operation manually, a burden placed on the operator is large, and performing the operation at a time may cause aspiration or abnormality in heartbeat or respiration. In the seventh mode, in a case where the user is in the postprandial state, the "lowering" operation is performed at low speed. Then, after the "lowering" operation is temporarily stopped, any abnormality in heartbeat or respiration is detected, and, if there are no detected abnormality in heartbeat or respiration, the "lowering" operation is continued.

[S7001], [S7002], and [S7003]

The user selects the seventh mode via the first user interface 4, performs setting concerning the presence or absence of the postprandial state, and performs a lowering manipulation.

[S7004]

The body motion detector 2 receives the seventh mode, information about the presence of absence of the postprandial state, and a signal A related to the "lowering" manipulation.

[S7005]

The body motion detector 2 performs a postprandial state determination based on the received signal A. Specifically, a threshold period of time for defining the "postprandial state" is previously stored in the second memory 23, and the body motion detector 2 compares eating information about the user with the current time and determines whether the current time is within the threshold period of time. Then, when determining that the current time is within the threshold period of time, the body motion detector 2 determines that the user is in the "postprandial state" (YES in step S7005). Moreover, when determining that the current time is not within the threshold period of time, in other words, a sufficient amount of time has elapsed, the body motion detector 2 determines that the user is not in the "postprandial state" (NO in step S7005).

When the body motion detector 2 determines that the user is "not in the postprandial state" (NO in step S7005), the bed system performs the "lowering" operation which is equivalent to steps S5012 to S5014.

[S7006], [S7007], and [S7008]

When the body motion detector 2 determines that the user is "in the postprandial state" (YES in step S7005), the bed system performs an operation similar to steps S1005 to S1007.

[S7009]

The body motion detector 2 determines whether there is a presage of abnormality in heartbeat or respiration of the user. Specifically, a threshold value for heartbeat rate or respiratory rate is previously stored in, for example, the second memory 23, and, when determining that the heartbeat rate or respiratory rate of the user exceeds the threshold value, the body motion detector 2 determines that there is a "presage of abnormality".

[S7010]

When determining that there is no presage of abnormality in heartbeat or respiration of the user (NO in step S7009), the body motion detector 2 performs an operation similar to step S1009. When determining that the second condition is not satisfied (NO in step S7010), the first controller 101 repeats step S7006.

[S7011]

When determining that the second condition is satisfied (YES in step S7010), the body motion detector 2 performs an operation similar to step S1010. When determining that the section is in the second position (YES in step S7011), the body motion detector 2 ends the operation.

[S7012]

When the body motion detector 2 determines that the section is not in the second position (NO in step S7011), the first controller 101 performs step S1011.

[S7013]

The first controller 101 performs step S1012.

When determining that the third time has not yet elapsed (NO in step S7013), the first controller 101 repeats step S7012.

[S7014]

When the first controller 101 determines that the third time has elapsed (YES in step S7013), the body motion detector 2 performs an operation similar to step S7009.

[S7015]

When determining that there is no presage of abnormality in heartbeat or respiration of the user (NO in step S7014), the body motion detector 2 performs an operation similar to step S1014. When determining that the third condition is satisfied (YES in step S7015), the first controller 101 repeats step S7006. When determining that the third condition is not satisfied (NO in step S7015), the first controller 101 repeats step S7012.

[S7016]

When the body motion detector 2 determines that there is a presage of abnormality in heartbeat or respiration of the user (YES in step S7014), the first controller 101 performs an operation similar to step S1007. Furthermore, here, the first controller 101 does not necessarily need to perform perfect stopping, but can perform the "lowering" operation at low speed.

[S7017]

The first controller 101 determines whether an eleventh time has elapsed from step S7016. When determining that the eleventh time has not yet elapsed (NO in step S7017), the first controller 101 repeats step S7016. When determining that the eleventh time has elapsed (YES in step S7017), the first controller 101 repeats step S7015.
[S7018]
When the body motion detector 2 determines that there is a presage of abnormality in heartbeat or respiration of the user (YES in step S7009), the first controller 101 performs an operation similar to step S1007. Furthermore, here, the first controller 101 does not necessarily need to perform perfect stopping, but can perform the "lowering" operation at low speed.
[S7019]
The first controller 101 determines whether an eleventh time has elapsed from step S7018. When determining that the eleventh time has not yet elapsed (NO in step S7019), the first controller 101 repeats step S7018. When determining that the eleventh time has elapsed (YES in step S7019), the body motion detector 2 repeats step S7009.

<5-2> Advantageous Effects in Seventh Mode

As described above, in the seventh mode, an operation is appropriately performed based on the status of eating of the user. This enables preventing aspiration after eating, enables appropriately coping with a case where there is a presage of abnormality in heartbeat or respiration, and also enables reducing a burden on the operator.

Moreover, in the fifth embodiment, with respect to portions similar to those in the first and second embodiments, similar advantageous effects are able to be obtained.

<6> Sixth Embodiment

A sixth embodiment is described. In the first embodiment, automatic driving for prompting falling asleep has been described. In the sixth embodiment, a method of appropriately performing automatic driving in conformity with the status of the user. Furthermore, the basic configuration and basic operation of the bed system according to the sixth embodiment are similar to those of the bed system according to the above-described first embodiment. Accordingly, descriptions about particulars described in the above-described first embodiment and particulars which are able to be easily analogized from the above-described first embodiment are omitted here.

<6-1> Eighth Mode

Figure 15:
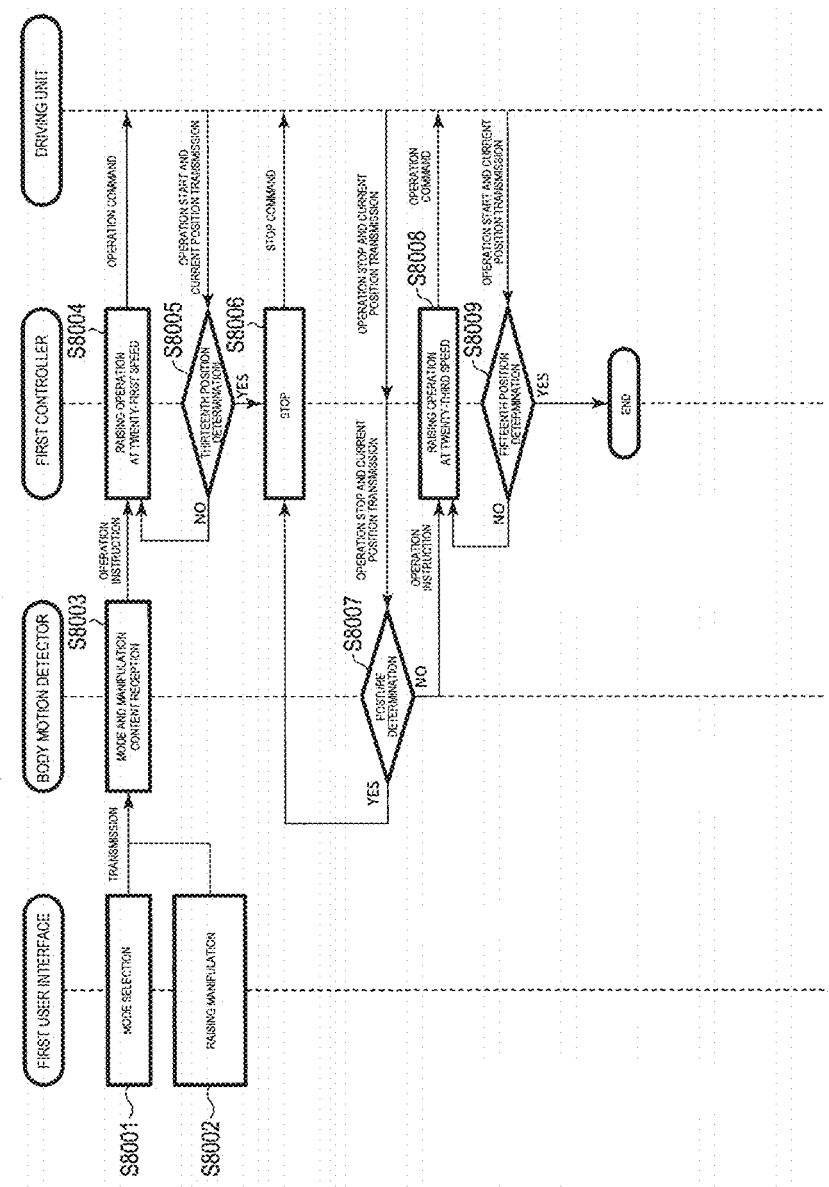
FIG. 15 is a flowchart illustrating an operation in an eighth mode of the bed system.

An eighth mode in the bed system according to the present embodiment is described with use of FIG. 15. The eighth mode is a mode which is used when automatic driving for assisting an on-bed sitting square of the user is performed.

The eighth mode is a mode in which, first, back raising for the user is performed and, after the user puts the user's legs down from the bed and comes into a sitting square posture, the back is further raised.
[S8001] and [S8002]
The user selects the eighth mode via the first user interface 4, and performs the raising manipulation.
[S8003]
The body motion detector 2 receives the eighth mode and a signal A concerning the "raising" manipulation. Then, the body motion detector 2 transmits a signal C for performing the raising operation at a twenty-first speed.
[S8004]
In response to receiving the signal C, the first controller 101 causes the driving unit to perform the raising operation at the twenty-first speed.

[S8005]
The first controller 101 determines whether the section is in a thirteenth position (the inclination angle $\theta 1 = \alpha 8°$). The first controller 101 repeats step S8004 until the section reaches the thirteenth position.
[S8006]
When determining that the section reaches the thirteenth position, the first controller 101 stops the "raising" operation. Furthermore, the first controller 101 does not necessarily need to perform stopping but can perform the raising operation at a twenty-second speed (lower than the twenty-first speed).
[S8007]
The body motion detector 2 determines a posture of the user. Specifically, the body motion detector 2 determines whether the user has put the user's legs down from the bed and come into a sitting square posture (on-bed sitting square) and the section is in a fourteenth position (the inclination angle $\theta 1 = \beta 8°$, where $\alpha 8 < \beta 8$). When determining that the user has come into the on-bed sitting square and the section is in the fourteenth position (YES in step S8007), the first controller 101 repeats step S8006.

The present embodiment is not limited to this case, and, for example, in step S8007, the body motion detector 2 can be configured not to determine whether the section is in the fourteenth position but to determine only the posture of the user.
[S8008]
When determining that the user has not come into the on-bed sitting square (NO in step S8007), the body motion detector 2 transmits a signal C for performing the raising operation at a twenty-third speed (which can be almost equal to the twenty-first speed, can be lower than or higher than the twenty-first speed, and is higher than the twenty-second speed). In response to this, the first controller 101 causes the driving unit to perform the raising operation at the twenty-third speed based on the signal C.
[S8009]
The first controller 101 determines whether the section is in a fifteenth position (the inclination angle $\theta 1 = \gamma 8°$, where $\beta 8 < \gamma 8$). The first controller 101 repeats step S8008 until the section reaches the fifteenth position. When determining that the section has reached the fifteenth position, the first controller 101 ends the operation.

<6-2> Effects in Eighth Mode

As described above, in the eighth mode, it is possible to assist the user in coming into a posture of on-bed sitting square.

Moreover, in the sixth embodiment, with respect to portions similar to those in the first and second embodiments, similar advantageous effects are able to be obtained.

<6-3> Ninth Mode

Figure 16:
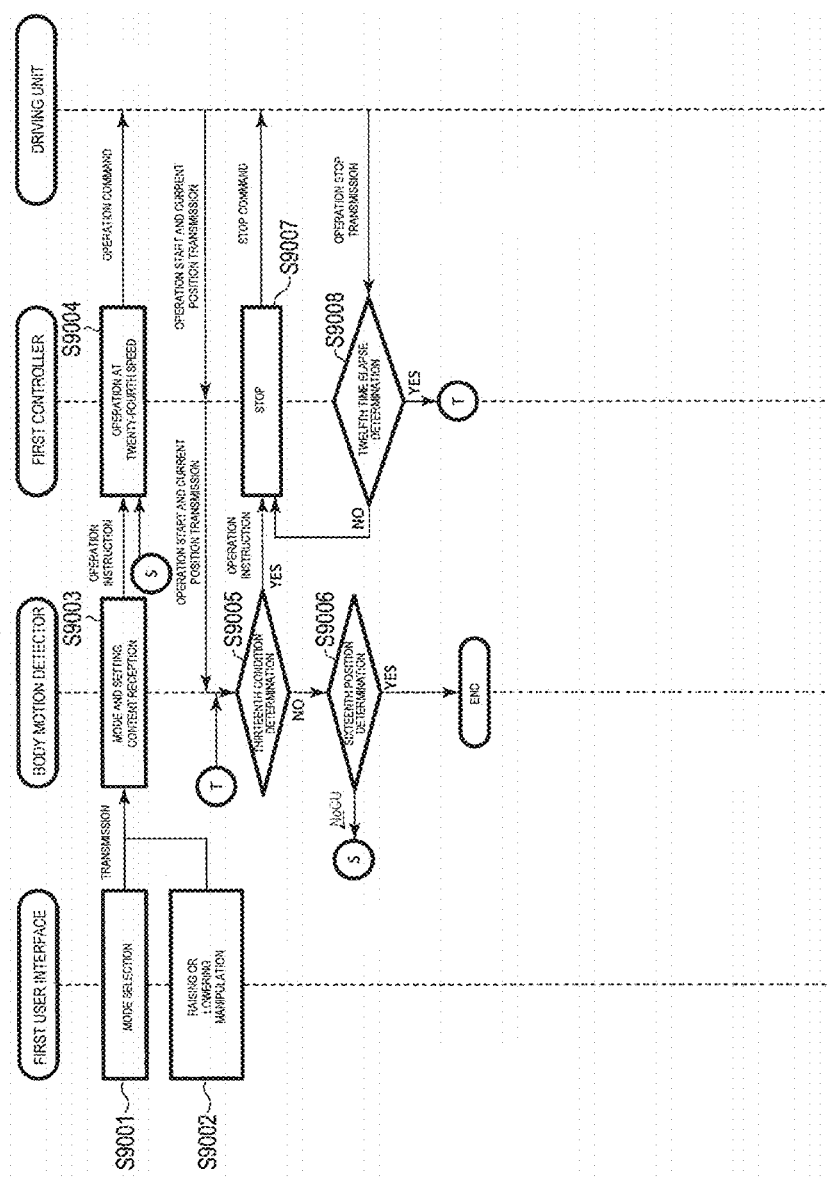
FIG. 16 is a flowchart illustrating an operation in a ninth mode of the bed system.

A ninth mode in the bed system according to the present embodiment is described with use of FIG. 16. The ninth mode is a mode for performing an operation at low speed in an optional condition.
[S9001] and [ S9002]
The user selects the ninth mode via the first user interface 4, and performs a raising manipulation or a lowering manipulation.
[S9003]
The body motion detector 2 receives the ninth mode and a signal A concerning the raising manipulation or the lowering manipulation. Then, the body motion detector 2 transmits a signal C for performing the operation at a twenty-fourth speed.

[S9004]

In response to receiving the signal C, the first controller 101 causes the driving unit to perform the operation at the twenty-fourth speed.

[S9005]

The body motion detector 2 determines whether a thirteenth condition (for example, any one of "the amount of change in heartbeat rate of the user exceeding a predetermined value", "the sleeping posture of the user being lying face-down", and "the value of a current flowing through the actuator exceeding a predetermined value") is satisfied.

[S9006]

When determining that the thirteenth condition is not satisfied (NO in step S9005), the body motion detector 2 determines whether the section is in a sixteenth position (optional position). When determining that the section is in the sixteenth position (YES in step S9006), the body motion detector 2 ends the operation. When the body motion detector 2 determines that the section is not in the sixteenth position (NO in step S9006), the first controller 101 repeats step S9004.

Furthermore, each time steps S9004 to S9006 are repeated, the sixteenth position can be updated. Specifically, the operation is performed in such a manner that, in the case of the raising manipulation, the sixteenth position is updated to the inclination angle $\theta 1=\alpha 9°$ ($0°<\alpha 9°$) and, in the case of the lowering manipulation, the sixteenth position is updated to the inclination angle $\theta 1=0°$.

[S9007]

When determining that the thirteenth condition is satisfied (YES in step S9005), the body motion detector 2 causes the first controller 101 to stop the operation. Furthermore, the first controller 101 does not necessarily need to perform stopping but can perform the operation at a twenty-fifth speed (lower than the twenty-fourth speed).

[S9008]

The first controller 101 determines whether a twelfth time has elapsed from step S9007. Furthermore, this step can be performed to determine not the time but the position of the section.

When determining that the twelfth time has not yet elapsed (NO in step S9008), the first controller 101 repeats step S9007.

When determining that the twelfth time has elapsed (YES in step S9008), the body motion detector 2 repeats step S9005.

<6-4> Effects in Ninth Mode

As described above, in the ninth mode, it is possible to perform the operation at low speed in an optional condition.

Furthermore, while a case where, in the ninth mode, the operation is caused to be performed at low speed in an optional condition has been described, the present embodiment is not limited to this. Specifically, the first controller 101 can perform such an operation as to set the back section 11 to a first angle (for example, 10°) in a case where the sleeping posture of the user is lying face-down, set the back section 11 to a second angle (for example, 20°) larger than the first angle in a case where the sleeping posture of the user is lying sideways, and set the back section 11 to a third angle (for example, 30°) larger than the second angle in a case where the sleeping posture of the user is lying face-up.

Moreover, in the sixth embodiment, with respect to portions similar to those in the first and second embodiments, similar advantageous effects are able to be obtained.

<7> Others

Furthermore, even in a case where an air mattress which is divided into a plurality of regions capable of being pneumatically controlled is employed as the mattress 3, the above-described embodiments can be applied. In a case where such an air mattress is employed as the mattress 3, it is favorable not to perform the "raising" operation or the "lowering" operation during a period when the internal pressure of the air mattress is adjusted.

Moreover, in each of the above-described embodiments, for example, each operation speed or each time can also be adjusted depending on the height of the mattress 3. For example, if the position of the mattress 3 is away from the floor, the user may get injured when falling. Therefore, for example, in a case where the position of the mattress 3 is high, it is favorable to decrease the operation speed or increase the period of time of a low-speed (or stopping) operation.

Moreover, in each of the above-described embodiments, for example, each operation speed or each time can also be adjusted depending on the body weight of the user (a load applied to the bed apparatus 1). For example, if the body weight of the user is large, the user may get injured when falling. Therefore, for example, in a case where the body weight of the user is large, it is favorable to decrease the operation speed or increase the period of time of a low-speed (or stopping) operation.

Moreover, some or all of the above-described modes can be used in combination.

Moreover, each of the speeds is set as a fixed speed, but can be changed according to a time axis. For example, each speed can be made gradually higher as time proceeds, and, after reaching a threshold value, each speed can be made gradually lower. Moreover, for example, the increase rate of each speed can be made mild at first in the time axis, the increase rate of each speed can be made sharp in progression, and the increase rate of each speed can be made mild after a given time is reached.

Furthermore, the above-described embodiments include the following aspects. Specifically,

[1]

A bed apparatus including:
- a supporting unit that supports a user; and
- a control unit that controls an operation of the supporting unit,
- wherein a speed of the operation of the supporting unit in a case where the user manipulates the supporting unit is higher than a speed at which the control unit automatically causes the supporting unit to operate.

[2] In the above [1],
- when causing the supporting unit to perform a first operation, the control unit causes the supporting unit to operate at a first speed, operate at a second speed lower than the first speed, and operate at a third speed higher than the second speed.

[3] In the above [2],
- when causing the supporting unit to perform the first operation, in a case of determining that the user has fallen asleep, the control unit causes the supporting unit to operate at the first speed.

[4] In the above [1],
when causing the supporting unit to perform a second operation, if detecting body motion, a heartbeat rate, or a respiratory rate of the user in a vicinity of time at which the user intends to sit up, the control unit causes the supporting unit to operate.

[5] In the above [4],
when causing the supporting unit to perform the second operation, in a case of determining that the user has fallen asleep again, if detecting body motion, a heartbeat rate, or a respiratory rate of the user in a vicinity of time at which the user intends to sit up, the control unit causes the supporting unit to operate.

[6] In the above [1],
when causing the supporting unit to perform a third operation, in a case where respiration of the user has become unsteady, the control unit causes the supporting unit to operate.

[7] In the above [6],
when causing the supporting unit to perform the second operation, the control unit checks a state of respiratory rate of the user after a given period of time elapses, and determines whether to cause the supporting unit to operate.

[8] In the above [1],
when the control unit causes the supporting unit to perform a fourth operation, an operation speed of the supporting unit in a case where the user is lying on the supporting unit is lower than an operation speed of the supporting unit in a case where the user is not lying on the supporting unit.

[9] In the above [1],
when the control unit causes the supporting unit to perform a fifth operation, an operation speed of the supporting unit in a case where a sufficient amount of time has not passed after the user eats is lower than an operation speed of the supporting unit in a case where the sufficient amount of time has passed after the user eats.

[10] In the above [9],
when causing the supporting unit to perform the fifth operation, in a case where the sufficient amount of time has not passed after the user eats, the control unit causes the supporting unit to operate, then causes the supporting unit to temporarily stop, determines any abnormality in heartbeat or respiration of the user, and, if there is no abnormality in heartbeat or respiration, causes the supporting unit to operate.

[11] In the above [1],
when the control unit causes the supporting unit to perform a sixth operation, an operation speed of the supporting unit in a case where a posture of the user on the supporting unit is a first posture is higher than an operation speed of the supporting unit in a case where the posture of the user on the supporting unit is a second posture.

[12] In the above [1],
when the control unit causes the supporting unit to perform a seventh operation, an operation speed of the supporting unit in a case where an amount of change in heartbeat rate of the user exceeds a predetermined value is lower than an operation speed of the supporting unit in a case where the amount of change in heartbeat rate of the user does not exceed the predetermined value.

[13] In the above [1],
when the control unit causes the supporting unit to perform an eighth operation, an operation speed of the supporting unit in a case where a sleeping posture of the user is lying face-down is lower than an operation speed of the supporting unit in a case where the sleeping posture of the user is not lying face-down.

[14] In the above [1],
when causing the supporting unit to perform a ninth operation, the control unit sets the supporting unit to a first angle in a case where a sleeping posture of the user is lying face-down, sets the supporting unit to a second angle larger than the first angle in a case where the sleeping posture of the user is lying sideways, and sets the supporting unit to a third angle larger than the second angle in a case where the sleeping posture of the user is lying face-up.

[15] In the above [1],
when the control unit causes the supporting unit to perform a tenth operation, an operation speed of the supporting unit in a case where a value of a current flowing through an actuator which causes the supporting unit to operate exceeds a predetermined value is lower than an operation speed of the supporting unit in a case where the value of a current flowing through the actuator does not exceed the predetermined value.

[16] In the above [3],
the bed apparatus further includes a user interface used for the user to issue an instruction for operation to the control unit,
wherein, in a case where an icon concerning falling asleep is selected by the user, the user interface causes the control unit to perform the first operation.

[17] In the above [4], the bed apparatus further includes a user interface used for the user to issue an instruction for operation to the control unit,
wherein, in a case where an icon concerning automatic driving is selected by the user, the user interface causes the control unit to perform the second operation.

[18] In the above [6],
the bed apparatus further includes a user interface used for the user to issue an instruction for operation to the control unit,
wherein, in a case where an icon concerning respiration is selected by the user, the user interface causes the control unit to perform the third operation.

[19] In the above [8],
the bed apparatus further includes a user interface used for the user to issue an instruction for operation to the control unit,
wherein, in a case where an icon concerning a raising operation or a lowering operation is selected by the user, the user interface causes the control unit to perform the fourth operation.

[20] In the above [9],
the bed apparatus further includes a user interface used for the user to issue an instruction for operation to the control unit,
wherein, in a case where an icon concerning eating is selected by the user, the user interface causes the control unit to perform the fifth operation.

While embodiments of the present invention have been described above, the present invention is not limited to the above-described embodiments, and can be embodied in various modified manners within a range which does not depart from the gist thereof. Additionally, the above-described embodiments include inventions made in various phases, and various inventions are extracted by combining some of all of the disclosed constituent elements as appropriate. For example, even if some constituent elements are deleted from the disclosed constituent elements, as long as a predetermined advantageous effect is attainable, the remaining constituent elements can be extracted as an invention.

The invention claimed is:

1. A bed apparatus comprising:
a supporting unit capable of supporting a user; and
a controller configured to control a movement of the supporting unit,
wherein a speed of the movement of the supporting unit in a case where the user manipulates the supporting unit is higher than a speed at which the controller automatically causes the supporting unit to move, and
wherein the controller is configured to cause the support unit to perform a first continuous operation including
moving the supporting unit at a first speed in response to an angle of the supporting unit being greater than a first angle,
automatically changing the first speed to a second speed lower than the first speed during the first continuous operation in response to the angle of the supporting unit being less than the first angle and greater than a second angle, and
automatically changing the second speed to a third speed, higher than the second speed, in response to the angle of the supporting unit being less than the second angle.

2. The bed apparatus according to claim 1, wherein, when causing the supporting unit to perform the first continuous operation, the controller is configured to cause the supporting unit to move at the first speed, move at the second speed, and move at the third speed in order.

3. The bed apparatus according to claim 2, wherein, when causing the supporting unit to perform the first continuous operation, in a case of determining that the user has fallen asleep, the controller is configured to cause the supporting unit to move at the first speed.

4. The bed apparatus according to claim 1, wherein, when causing the supporting unit to perform a second operation, if detecting body motion, a heartbeat rate, or a respiratory rate of the user in a vicinity of time at which the user intends to sit up, the controller causes the supporting unit to move.

5. The bed apparatus according to claim 4, wherein, when causing the supporting unit to perform the second operation, in a case of determining that the user has fallen asleep again, if detecting body motion, a heartbeat rate, or a respiratory rate of the user in a vicinity of time at which the user intends to sit up, the controller causes the supporting unit to move.

6. The bed apparatus according to claim 5, wherein, when causing the supporting unit to perform the second operation, the controller checks a state of respiratory rate of the user after a given period of time elapses, and determines whether to cause the supporting unit to move.

7. The bed apparatus according to claim 4, further comprising a user interface used for the user to issue an instruction to the controller,
wherein, in a case where an icon concerning automatic driving is selected by the user, the user interface causes the controller to perform the second operation.

8. The bed apparatus according to claim 1, wherein, when causing the supporting unit to perform a third operation, in a case where respiration of the user has become unsteady, the controller causes the supporting unit to move.

9. The bed apparatus according to claim 8, further comprising a user interface used for the user to issue an instruction to the controller,
wherein, in a case where an icon concerning respiration is selected by the user, the user interface causes the controller to perform the third operation.

10. The bed apparatus according to claim 1, wherein, when the controller causes the supporting unit to perform a fourth operation, a speed of the movement of the supporting unit in a case where the user is lying on the supporting unit is lower than a speed of the movement of the supporting unit in a case where the user is not lying on the supporting unit.

11. The bed apparatus according to claim 10, further comprising a user interface used for the user to issue an instruction to the controller,
wherein, in a case where an icon concerning a raising operation or a lowering operation is selected by the user, the user interface causes the controller to perform the fourth operation.

12. The bed apparatus according to claim 1, wherein, when the controller causes the supporting unit to perform a fifth operation, a speed of the movement of the supporting unit in a case where a sufficient amount of time has not passed after the user eats is lower than a speed of the movement of the supporting unit in a case where the sufficient amount of time has passed after the user eats.

13. The bed apparatus according to claim 12, wherein, when causing the supporting unit to perform the fifth operation, in a case where the sufficient amount of time has not passed after the user eats, the controller causes the supporting unit to move, then causes the supporting unit to temporarily stop, determines any abnormality in heartbeat or respiration of the user, and, if there is no abnormality in heartbeat or respiration, causes the supporting unit to move.

14. The bed apparatus according to claim 12, further comprising a user interface used for the user to issue an instruction to the controller,
wherein, in a case where an icon concerning eating is selected by the user, the user interface causes the controller to perform the fifth operation.

15. The bed apparatus according to claim 1, wherein, when the controller causes the supporting unit to perform a sixth operation, a speed of the movement of the supporting unit in a case where a posture of the user on the supporting unit is a first posture is higher than a speed of the movement of the supporting unit in a case where the posture of the user on the supporting unit is a second posture.

16. The bed apparatus according to claim 1, wherein, when the controller causes the supporting unit to perform a seventh operation, a speed of the movement of the supporting unit in a case where an amount of change in heartbeat rate of the user exceeds a predetermined value is lower than a speed of the movement of the supporting unit in a case where the amount of change in heartbeat rate of the user does not exceed the predetermined value.

17. The bed apparatus according to claim 1, wherein, when the controller causes the supporting unit to perform an eighth operation, a speed of the movement of the supporting unit in a case where a sleeping posture of the user is lying face-down is lower than a speed of the movement of the supporting unit in a case where the sleeping posture of the user is not lying face-down.

18. The bed apparatus according to claim 1, wherein, when causing the supporting unit to perform a ninth operation, the controller sets the supporting unit to a first angle in a case where a sleeping posture of the user is lying face-down, sets the supporting unit to a second angle larger than the first angle in a case where the sleeping posture of the user is lying sideways, and sets the supporting unit to a third angle larger than the second angle in a case where the sleeping posture of the user is lying face-up.

19. The bed apparatus according to claim 1, wherein, when the controller causes the supporting unit to perform a tenth operation, a speed of the movement of the supporting unit in a case where a value of a current flowing through an actuator which causes the supporting unit to move exceeds a predetermined value is lower than a speed of the movement of the supporting unit in a case where the value of a current flowing through the actuator does not exceed the predetermined value.

20. The bed apparatus according to claim 1, further comprising a user interface used for the user to issue an instruction to the controller,
   wherein, in a case where an icon concerning falling asleep is selected by the user, the user interface causes the controller to perform the first continuous operation.

21. The bed apparatus according to claim 1, wherein the controller is further configured to cause the support unit to perform the first continuous operation in response to determining that the user has fallen asleep.

22. The bed apparatus according to claim 1, wherein the first continuous operation is a lowering operation.

23. The bed apparatus according to claim 1, wherein the angle of the supporting unit is measured between a back portion of the supporting unit and a lower leg portion of the support unit.

24. The bed apparatus according to claim 1, wherein the controller is further configured to cause the support unit to change from the first speed to the second speed in response to an elapsed time from a beginning of the first continuous operation being greater than a threshold.

* * * * *